(12) United States Patent
Bueno et al.

(10) Patent No.: US 12,317,796 B2
(45) Date of Patent: Jun. 3, 2025

(54) COMPOSITIONS AND METHODS FOR COTTON CELL CULTURE

(71) Applicant: GALY CO., Boston, MA (US)

(72) Inventors: Luciano Luiz Bueno, Boston, MA (US); Paula Maria Elbl, Boston, MA (US); Leticia Silveira De Sousa Luz, Boston, MA (US)

(73) Assignee: GALY CO., Boston, MA (US)

( * ) Notice: Subject to any disclaimer, the term of this patent is extended or adjusted under 35 U.S.C. 154(b) by 0 days.

(21) Appl. No.: 18/515,878

(22) Filed: Nov. 21, 2023

(65) Prior Publication Data

US 2024/0114863 A1  Apr. 11, 2024

Related U.S. Application Data

(63) Continuation of application No. 17/613,340, filed as application No. PCT/US2020/034413 on May 22, 2020, now abandoned.

(60) Provisional application No. 63/003,185, filed on Mar. 31, 2020, provisional application No. 62/852,160, filed on May 23, 2019.

(51) Int. Cl.
| | | |
|---|---|---|
| A01H 4/00 | (2006.01) | |
| A01H 5/02 | (2018.01) | |
| A01H 6/60 | (2018.01) | |
| D01F 13/02 | (2006.01) | |

(52) U.S. Cl.
CPC .............. *A01H 4/002* (2021.01); *A01H 4/001* (2013.01); *A01H 4/005* (2013.01); *A01H 5/02* (2013.01); *A01H 6/604* (2018.05); *D01F 13/02* (2013.01)

(58) Field of Classification Search
CPC ......... A01H 6/604; A01H 4/001; A01H 4/005
See application file for complete search history.

(56) References Cited

U.S. PATENT DOCUMENTS

| | | |
|---|---|---|
| 6,259,003 B1 | 7/2001 | Fujisawa et al. |
| 2001/0026939 A1 | 10/2001 | Rice et al. |
| 2003/0041351 A1 | 2/2003 | Kasukabe et al. |
| 2004/0049808 A1 | 3/2004 | Haigler et al. |
| 2011/0145947 A1 | 6/2011 | Pei et al. |
| 2015/0059023 A1 | 2/2015 | Yohn et al. |
| 2019/0008113 A1 | 1/2019 | Rathore et al. |
| 2020/0281149 A1 | 9/2020 | Spyrou |

FOREIGN PATENT DOCUMENTS

| | | |
|---|---|---|
| CN | 1748474 A | 3/2006 |
| CN | 103387621 A | 11/2013 |
| CN | 104109032 A | 10/2014 |
| EP | 0209882 A2 | 1/1987 |
| WO | 8905344 A1 | 6/1989 |
| WO | 9640924 A2 | 12/1996 |
| WO | 2005063002 A1 | 7/2005 |
| WO | 2016120889 A1 | 8/2016 |

OTHER PUBLICATIONS

Monts, R. "Comparative Characteristics of Bioreactors for In Vitro Cotton Culture," A Thesis in Chemical Engineering, Texas Tech University, May 1993.*
Rajasekaran,K. "Regeneration of plants from cryopreserved embryogenic cell suspension and callus cultures of cotton (*Gossypium hirsutum* L.)", Plant Cell Reports (1996) 15: 859-864.*
Bouchabke-Coussa et al., "Wuschel overexpression promotes somatic embryogenesis and induces organogenesis in cotton (*Gossypium hirsutum* L.) tissues cultured in vitro"; Plant Cell Rep, vol. 32, pp. 675-686 (2013).
Chavan et al., "Growth of Cotton fiber is enhanced by IAA and NAA under in vitro conditions"; International Journal of Current Microbiology and Applied Sciences; vol. 3, No. 7, pp. 558-563 (2014).
Fang et al., "Cotton fiber elongation network revealed by expression profiling of longer fiber lines introgressed with different Gossypium barbadense chromosome segments"; BMC Genomics, vol. 15, No. 838, pp. 1-15 (2014).
Feng et al., "A Novel Cotton Ovule Culture: Induction, Growth, and Characterization of Submerged Cotton Fibers (*Gossypium hirsutum* L.)"; In Vitro Cell. Dev. Biol.-Plant, vol. 36, pp. 293-299 (2000).
Gaspar et al., "Plant Hormones and Plant Growth Regulators in Plant Tissue Culture"; In Vitro Cell. Dev. Biol.-Plant, vol. 32, pp. 272-289 (1996).
Goldbeck et al., "Construction of pOGOduet—An inducible, bicistronic vector for synthesis of recombinant proteins in Corynebacterium glutamicum"; Plasmid, vol. 95, pp. 11-15 (2018).
Graves et al., "Chronology of the differentiation of cotton (*Gossypium hirsutum* L.) fiber cells"; Planta, vol. 175, pp. 254-258 (1988).
Kim et al., "Cotton Fiber Growth in Planta and in Vitro. Models for Plant Cell Elongation and Cell Wall Biogenesis"; Plant Physiology, vol. 127, pp. 1361-1366 (2001).
Montes, "Comparative Characterization of Bioreactors for in Vitro Cotton Culture"; Thesis in Chemical Engineering; Texas Tech University; pp. i-vii and 1-87 (1993).
Nayyar et al., "Hormonal Regulation of Cotton Fibre Elongation in *Gossypium arboreum* L. in vitro and in vivo"; Biochem. Physiol. Pflanzen, vol. 185, pp. 415-421 (1989).

(Continued)

Primary Examiner — Susan McCormick Ewoldt
(74) Attorney, Agent, or Firm — EVENTIDE LAW LLC

(57) ABSTRACT

A method of producing cotton fibers from cotton callus cells in vitro is provided. The method includes the following steps in order: (1) culturing cotton callus cells in a suspension culture medium; (2) feeding a first bioreactor with the callus cells, a multiplication medium, and air compression; (3) culturing the callus cells in the first bioreactor for 5 to 12 days to accomplish at least two rounds of duplication of the callus cells; (4) serially repeating steps (2) and (3) one or more times, thereby obtaining serially duplicated cells; (5) seeding one or more second bioreactors with the serially duplicated cells, an elongation medium, and air compression; (6) culturing the serially duplicated cells in the one or more second bioreactors, thereby obtaining elongated cells; and (7) culturing the elongated cells in a maturation medium, thereby obtaining the cotton fibers.

12 Claims, 2 Drawing Sheets

(56) References Cited

OTHER PUBLICATIONS

Pierce et al., "Cultures of Gossypium barbadense cotton ovules offer insights into the microtubule-mediated control of fiber cell expansion"; Planta, vol. 249, pp. 1551-1563 (2019).

Rajasekaran, "Regeneration of plants from cryopreserved embryogenic cell suspension and callus cultures of cotton (*Gossypium hirsutum* L.)"; Plant Cell Reports, vol. 15, pp. 859-864 (1996).

Triplett et al., "Ovule and Suspension Culture of a Cotton Fiber Development Mutant"; in Vitro Cellular~Developmental Biology, vol. 25, No. 2, pp. 197-200 (1989).

Trolinder et al., "Differentiation of Cotton Fibers From Single Cells in Suspension Culture"; in Vitro Cellular & Developmental Biology, vol. 23, No. 11, pp. 789-794 (1987).

Zhang et al., "Developmental and hormonal regulation of fiber quality in two natural-colored cotton cultivars"; ScienceDirect—Journal of Integrative Agriculture, vol. 16, No. 8, pp. 1720-1929 (2017).

Xiao et al., "A Pivotal Role of Hormones in Regulating Cotton Fiber Development"; Frontiers in Plant Science, vol. 10, No. 87, pp. 1-10 (2019).

* cited by examiner

COMPOSITIONS AND METHODS FOR COTTON CELL CULTURE

CROSS-REFERENCE

This application is a continuation of U.S. application Ser. No. 17/613,340, filed Nov. 22, 2021, now abandoned, which is a national stage application of International Appl. PCT/US2020/034413, filed May 22, 2020, and which claims the benefit of U.S. Provisional Patent Application No. 63/003,185 filed on Mar. 31, 2020, and U.S. Provisional Patent Application No. 62/852,160, filed on May 23, 2019, all of which are hereby incorporated by reference.

BACKGROUND

In vitro production of plant cell compositions can overcome a number of limiting factors associated with in planta production of plant-derived products, thereby providing a reliable, energy-efficient, and eco-friendly alternative to traditional agriculture. For example, plant cell compositions produced in vitro can be continuously available, while crops grown in planta are often subject to a cyclic availability. However, the speed and scale of in vitro production of plant cell compositions currently remain limited by a number of engineering constraints, such as the difficulties of preparing a sufficient amount of cell inoculum of sufficient cellular homogeneity or the lack of streamlined protocols for an in vitro plant cell production cycle.

SUMMARY

Provided herein are methods for preparing a plant cell composition, comprising: (a) contacting a plant callus with a callus growth medium under conditions sufficient to produce a proliferating cell aggregate; and (b) contacting the proliferating cell aggregate with a cell culture medium under conditions sufficient to produce the plant cell composition comprising at least $1\times10^3$ cells, where cells of the plant cell composition are characterized by at least two of (i)-(iii): (i) at least 70% of the cells have a cell size of 100 microns (μm) or less; (ii) at least 70% of the cells have a cytoplasmic optical density greater than a cytoplasmic optical density of a corresponding non-dividing cell; and (iii) at least 70% of the cells have a vacuole having a dimension of 3 microns (μm) to 8 μm. In some aspects, cells of the plant cell composition are configured to derive a pigment molecule, a flavor molecule, a pungent food additive, a sweetening molecule, or a fruit. In some aspects, cells of the plant cell composition are configured to derive a trichome, a hair-like structure, or a fiber. In some aspects, the plant cell composition is a cotton plant cell composition.

In some aspects, the plant cell composition comprises at least $1\times10^4$ cells. In further aspects, the plant cell composition comprises at least $1\times10^6$ cells. In further aspects, the plant cell composition comprises at least $1\times10^8$ cells. In further aspects, the plant cell composition comprises at least $1\times10^9$ cells. In some aspects, the cells of the plant cell composition are characterized by all of (i)-(iii). In some aspects, the plant cell composition has a distribution of cell size that is narrower than the proliferating cell aggregate. In some aspects, the plant cell composition has a distribution of cell cytoplasmic optical density that is narrower than the proliferating cell aggregate. In some aspects, the plant cell composition has a distribution of cell vacuole size that is narrower than the proliferating cell aggregate. In some aspects, the plant cell composition is in an exponential growth phase. In some aspects, the exponential growth phase is determined by a cell viability assay. In some aspects, the cell viability assay determines a cytoplasmic level of diphenol compounds. In some aspects, in (i), the cell size of the at least 70% of the cells is 80 μm or less. In some aspects, the cell size is determined by a microscope. In some aspects, the cell size of the at least 70% of the cells is of from 10 μm to 60 μm. In some aspects, at least 80% of the cells of the plant cell composition have a cell size of 100 μm or less. In some aspects, at least 90% of the cells of the plant cell composition have a cell size of 100 μm or less. In some aspects, in (ii), the cytoplasmic optical density is from 0.4 to 0.6. In some aspects, cytoplasmic optical density is determined by a spectrophotometer at a wavelength of from 180 nanometers (nm) to 800 nm. In some aspects, the wavelength is of from 200 nm to 700 nm. In some aspects, at least 80% cells of the plant cell composition have a cytoplasmic optical density greater than a cytoplasmic optical density of a corresponding non-dividing cell. In some aspects, at least 90% cells of the plant cell composition have a cytoplasmic optical density greater than a cytoplasmic optical density of a corresponding non dividing cell. In some aspects, in (iii), at least 80% of the cells of the plant cell composition have a vacuole having a dimension of 3 microns (μm) to 8 μm. In some aspects, the dimension of the vacuole is determined by a microscope. In some aspects, at least 90% of the cells of the plant cell composition have a vacuole having a dimension of 3 μm to 8 μm. In some aspects, the callus growth medium comprises at least four plant hormones or growth regulators. In some aspects, the at least four plant hormones or growth regulators of the callus growth medium are selected from the group consisting of indole acetic acid (IAA), indoyl-3-acrylic acid, 4-Cl-indoyl-3-acetic acid, indoyl-3-acetylaspartate, indole-3-acetaldehyde, indole-3-acetonitrile, indole-3-lactic acid, indole-3-propionic acid, indole-3-pyruvic acid, indole butyric acid (IBA), 2,4-dichlorophenoxyacetic acid (2,4-D), tryptophan, phenylacetic acid (PAA), glucobrassicin, naphthaleneacetic acid (NA A), picloram (PIC), dicamba, ethylene, para-chlorophenoxyacetic acid (pCPA), β-naphthoxyacetic acid (NOA), benzo(b)selenienyl-3 acetic acid, 2-benzothiazole acetic acid (BOTA), N6-(2-isopentenyl) adenine (2iP), zeatin (ZEA), dihydro-zeatin, zeatin riboside, kinetin (KIN), 6-(benzyladenine)-9-(2-tetrahydropyranyl)-9H-purine, 2,4,5,-trichlorophenoxy acetic acid (2,4,5-T), 6-benzylaminopurine (6BA), 1,3-diphenylurea, N-(2-chloro-4-pyridyl)-N'-phenylurea, (2,6-dichloro-4-pyridyl)-N'-phenylurea, N-phenyl-N'-1,2,3-thiadiazol-5-ylurea, gibberellin $A_5$, gibberellin A1 (GA1), gibberellic acid (GA3), gibberellin A4 (GA4), gibberellin A7 (GA7), brassinolide (BR), jasmonic acid (JA), gibberellin $A_8$, gibberellin $A_{32}$, gibberellin $A_9$, 15-β-OH-gibberellin A3, 15-β-OH-gibberellin $A_5$, 12-β-OH-gibberellin $A_5$, 12-α-gibberellin $A_5$, salicylic acid, (−) jasmonic acid, (+)-7-iso-jasmonic acid, putrescine, spermidine, spermine, oligosaccharins, and stigmasterol. In some aspects, the at least four plant hormones or growth regulators of the callus growth medium are selected from the group consisting of indole acetic acid (IAA), indole butyric acid (IBA), 2,4-dichlorophenoxyacetic acid (2,4 D), naphthaleneacetic acid (NAA), para-chlorophenoxyacetic acid (pCPA), β-naphthoxyacetic acid (NOA), 2-benzothiazole acetic acid (BTOA), picloram (PIC), 2,4,5,-trichlorophenoxyacetic acid (2,4,5-T), phenylacetic acid (PAA), kinetin (KIN), 6-benzylaminopurine (6BA), N6-(2-isopentenyl) adenine (2iP), zeatin (ZEA), gibberellin A1 (GA1), gibberellic acid (GA3), gibberellin A4 (GA4), gibberellin A7 (GA7), ethylene, brassinolide (BR), and jasmonic acid (JA). In some aspects, the callus growth medium is not a liquid at 25° C. In some aspects, the callus growth medium is agar-free. In some aspects, the callus growth medium has a pH of from 5.3 to 6.3. In some aspects, (a) comprises subculturing the plant callus for at least two passages on the callus growth medium. In some aspects, the at least two passages in (a) comprises from two to ten passages. In some aspects, each of the at least two passages in (a) is performed at a temperature of from 22° C. to 34° C. In some aspects, each of the at least two passages in (a) has a duration of from 15 to 32 days. In some aspects, cells of the proliferating cell aggregate divide at a rate greater than a cell division rate of remaining cells in the plant callus. In some aspects. (b) comprises subculturing the proliferating cell aggregate for at least two passages in the cell culture medium. In some aspects, the at least two passages in (b) comprises from two to ten passages. In some aspects, each of the at least two passages in (b) is performed at a temperature from 28° C. to 40° C. In some aspects, each of the at least two passages in (b) is performed at a temperature higher than that at which at least one passage of the at least two passages in (a) is performed. In some aspects, each of the at least two passages in (b) is performed at a temperature from 2° C. to 6° C. higher than that at which a passage of the at least two passages in (a) is performed. In some aspects, each of the at least two passages in (b) has a duration of from 10 days to 25 days. In some aspects, in (b), the cell culture medium comprises an enzyme that degrades a plant cell wall of a plant cell of the proliferating cell aggregate. In some aspects, the cell culture medium has a pH of from 5.3 to 6.3. In some aspects, the pH of the cell culture medium differs from a pH of the callus growth medium by less than 0.2 units. In some aspects, (b) comprises sieving, filtering, separating, pipetting, or decanting cells of the proliferating cell aggregate or a derivative thereof to yield the plant cell composition. In some aspects, the method further comprises, prior to (a): (c) contacting a plant explant with a callus induction medium under conditions sufficient to produce the plant callus. In some aspects, the plant explant comprises one or more members selected from the group consisting of apical meristem, cotyledon, young leaf, hypocotyl, ovule, stem, mature leaf, flower, flower stalk, root, bulb, germinated seed, and cambial meristematic cell (CMC). In some aspects, the plant explant comprises cambial meristematic cell (CMC). In some aspects, the callus induction medium is configured to facilitate division of at least a subset of cells of the plant explant. In some aspects, the callus induction medium comprises a diluted basal medium. In some aspects, the callus induction medium is not a liquid at 25° C. In some aspects, the callus induction medium is agar-free. In some aspects, the callus induction medium has a pH of from 5.3 to 6.3.

Also provided herein are methods for producing cotton, comprising: (a) providing a reaction vessel comprising a solution comprising a plurality of cotton cells; and (b) in the reaction vessel, contacting the solution with an elongation medium under conditions sufficient to induce at least a portion of the plurality of cotton cells to elongate to yield a plurality of elongated cotton cells, thereby producing the cotton having a dry mass of at least 10 grams per liter (g/L) fresh weight (FW), where an elongated cell of the plurality of elongated cotton cells has a first dimension that is greater than a second dimension of the elongated cell. In some aspects, The method of claim 1, where the dry mass of the cotton is at least 50 grams per liter (g/L) fresh weight (FW). In some aspects, the dry mass of the cotton is at least 100 grams per liter (g/L) fresh weight (FW). In some aspects, the dry mass of the cotton is from 50 grams per liter (g/L) fresh weight (FW) to 500 g/L (FW). In some aspects, the dry mass of the cotton is from 100 grams per liter (g/L) fresh weight (FW) to 500 g/L (FW). In some aspects, the dry mass of the cotton is from 100 grams per liter (g/L) fresh weight (FW) to 300 g/L (FW). In some aspects, the cotton comprises at most 10% by dry weight of a trash content. In some aspects, the cotton comprises at most 5% by dry weight of a trash content. In some aspects, the cotton comprises at most 1% by dry weight of a trash content. In some aspects, the cotton comprises at most 0.5% by dry weight of a trash content. In some aspects, the cotton comprises at most 0.1% by dry weight of a trash content. In some aspects, the trash content is a non-lint substance.

Also provided herein are methods for producing cotton, comprising: (a) providing a reaction vessel comprising a solution comprising a plurality of cotton cells; and (b) in the reaction vessel, contacting the solution with an elongation medium under conditions sufficient to induce at least a subset of the plurality of cotton cells to elongate to yield a plurality of elongated cotton cells, thereby producing the cotton, where an elongated cell of the plurality of elongated cotton cells has a first dimension that is greater than a second dimension of the elongated cell, where: (a)-(b) are performed in a time period of at most 45 days. In some aspects, the time period is at most 41 days. In some aspects, the time period is at most 34 days. In some aspects, the time period is at most 30 days. In some aspects, the cotton comprises at most 10% by dry weight of a trash content. In some aspects, the cotton comprises at most 5% by dry weight of a trash content. In some aspects, the cotton comprises at most 1% by dry weight of a trash content. In some aspects, the cotton comprises at most 0.5% by dry weight of a trash content. In some aspects, the cotton comprises at most 0.1% by dry weight of a trash content. In some aspects, the trash content is a non-lint substance. In some aspects, the method further comprises: (c) subjecting the plurality of elongated cotton cells to conditions sufficient to mature the plurality of elongated cotton cells to yield the cotton. In some aspects, (c) comprises contacting the plurality of elongated cotton cells with a maturation medium under conditions sufficient to yield a plurality of mature elongated cotton cells. In some aspects, (c) further comprises drying the plurality of mature elongated cotton cells to yield the cotton. In some aspects, (b) further comprises separating the plurality of elongated cells from a remainder of the plurality of cotton cells or a derivative thereof. In some aspects, the separating comprises filtering, sieving, decanting, centrifuging, or a combination thereof. In some aspects, the method further comprises removing the remainder of the plurality of cotton cells. In some aspects, the method further comprises recycling at least a portion of the remainder of the plurality of cotton cells. In some aspects, a cotton cell of the remainder of the plurality of cotton cells has a dimension that is less than the first dimension. In some aspects, the elongation medium is configured to facilitate release of a phenolic compound from a vacuole of at least one cotton cell of the plurality of cotton cells. In some aspects, the elongation medium comprises at least two plant hormones or growth regulators. In some aspects, the at least two plant hormones or growth regulators of the elongation medium are selected from the group consisting of indole acetic acid (IAA), indoyl-3-acrylic acid, 4-Cl-indoyl-3-acetic acid, indoyl-3-acetylaspartate, indole-3-acetaldehyde, indole-3-acetonitrile, indole-3-lactic acid, indole-3-propionic acid, indole-3-pyruvic acid, indole butyric acid (IBA), 2,4-dichlorophenoxyacetic acid (2,4-D), tryptophan, phenylacetic acid (PAA), glucobrassicin, naphthaleneacetic acid (NAA), picloram (PIC), dicamba, ethylene, para-chlorophenoxyacetic acid (pCPA), β-naphthoxyacetic acid (NOA), benzo(b)selenienyl-3 acetic acid, 2-benzothiazole acetic acid (BITOA), N6-(2-isopentenyl) adenine (2iP), zeatin (ZEA), dihydro-zeatin, zeatin riboside, kinetin (KIN), 6-(benzyladenine)-9-(2-tetrahydropyranyl)-9H-purine, 2,4,5,-trichlorophenoxyacetic acid (2,4,5-T), 6-benzylaminopurine (6BA), 1,3-diphenylurea, N-(2-chloro-4-pyridyl)-N'-phenylurea, (2,6-dichloro-4-pyridyl)-N'-phenylurea, N-phenyl-N'-1,2,3-thiadiazol-5-ylurea, gibberellin $A_5$, gibberellin A1 (GA1), gibberellic acid (GA3), gibberellin A4 (GA4), gibberellin A7 (GA7), brassinolide (BR), jasmonic acid (JA) gibberellin $A_8$, gibberellin $A_{32}$, gibberellin $A_9$, 15-β-OH-gibberellin $A_3$, 15-β-OH-gibberellin $A_5$, 12-β-OH-gibberellin $A_5$, 12-α-gibberellin $A_5$, salicylic acid, (−) jasmonic acid, (+)-7-iso-jasmonic acid, putrescine, spermidine, spermine, oligosaccharins, and stigmasterol. In some aspects, the at least two plant hormones or growth regulators of the elongation medium are selected from the group consisting of indole acetic acid (IAA), indole butyric acid (IB A), 2,4-dichlorophenoxyacetic acid (2,4 D), naphthaleneacetic acid (NAA), para-chlorophenoxyacetic acid (pCPA), β-naphthoxyacetic acid (NOA), 2-benzothiazole acetic acid (BTOA), picloram (PIC), 2,4,5-trichlorophenoxyacetic acid (2,4,5-T), phenylacetic acid (PAA), kinetin (KIN), 6-benzylaminopurine (6BA), N6-(2-isopentenyl) adenine (2iP), zeatin (ZEA), gibberellin A1 (GA1), gibberellic acid (GA3), gibberellin A4 (GA4), gibberellin A7 (GA7), ethylene, brassinolide (BR), and jasmonic acid (JA). In some aspects, the elongation medium has a pH of from 5.3 to 6.3. In some aspects, (b) is performed at a temperature of from 28° C. to 40° C. In some aspects, the cotton comprises at least 90% by dry weight cotton fibers. In some aspects, the cotton fibers comprise at most 10% by dry weight a short fiber content (SFC). In some aspects, the cotton fibers have an average fiber length of from 1.1 centimeter (cm) to 4.0 cm. In some aspects, the cotton fibers have a length uniformity of at least 70%. In some aspects, the cotton fibers have an average thickness of a secondary wall of at least 4 microns (μm). In some aspects, the cotton fibers comprise, by dry weight, 88% to 96% cellulose, 1.1% to 1.9% protein, and 0.7% to 1.2% pectic substance. In some aspects, the cotton fibers further comprise, by dry weight, 0.7% to 1.6% ash, 0.4% to 1.0% wax, 0.1% to 1.0% sugar, and 0.5% to 1.0% organic acid. In some aspects, the cellulose comprise at least 80% by dry weight crystalline cellulose as measured by X-ray diffraction. In some aspects, the cotton fibers have an average strength of at least 70 Mpsi as measured by a zero gauge Pressley test. In some aspects, the cotton fibers have an average strength of at least 15 g/tex as measured by a ⅛-inch gauge Pressley test. In some aspects, the cotton fibers have an average strength of at least 15 g/tex as measured by a ⅛-inch gauge high volume instrument (HVI) test.

Also provided herein are compositions comprising an engineered cotton comprising at most 10% by dry weight a trash content (TC). In some aspects, the engineered cotton comprises at most 8% by dry weight of a trash content. In some aspects, the engineered cotton comprises at most 5% by dry weight of a trash content. In some aspects, the engineered cotton comprises at most 2% by dry weight of a trash content. In some aspects, the engineered cotton comprises at most 1% by dry weight of a trash content. In some aspects, the engineered cotton comprises at most 0.5% by dry weight of a trash content. In some aspects, the engineered cotton comprises at most 0.2% by dry weight of a trash content. In some aspects, the engineered cotton comprises at most 0.1% by dry weight of a trash content. In some aspects, the trash content is a non-lint substance. In some aspects, the engineered cotton comprises at least 90% by dry weight cotton fibers. In some aspects, the cotton fibers comprise at most 10% by dry weight a short fiber content (SFC). In some aspects, the cotton fibers have an average fiber length of from 1.1 centimeter (cm) to 4.0 cm. In some aspects, the cotton fibers have a length uniformity of at least 70%. In some aspects, the cotton fibers have an average thickness of a secondary wall of at least 4 microns (μm). In some aspects, the cotton fibers comprise, by dry weight, 88% to 96% cellulose, 1.1% to 1.9% protein, and 0.7% to 1.2% pectic substance. In some aspects, the cotton fibers further comprise, by dry weight, 0.7% to 1.6% ash, 0.4% to 1.0% wax, 0.1% to 1.0% sugar, and 0.5% to 1.0% organic acid. In some aspects, the cellulose comprise at least 80% by dry weight crystalline cellulose as measured by X-ray diffraction. In some aspects, the cotton fibers have an average strength of at least 70 Mpsi as measured by a zero gauge Pressley test. In some aspects, the cotton fibers have an average strength of at least 15 g/tex as measured by a ⅛-inch gauge Pressley test. In some aspects, the cotton fibers have an average strength of at least 15 g/tex as measured by a ⅛-inch gauge high volume instrument (HVI) test.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
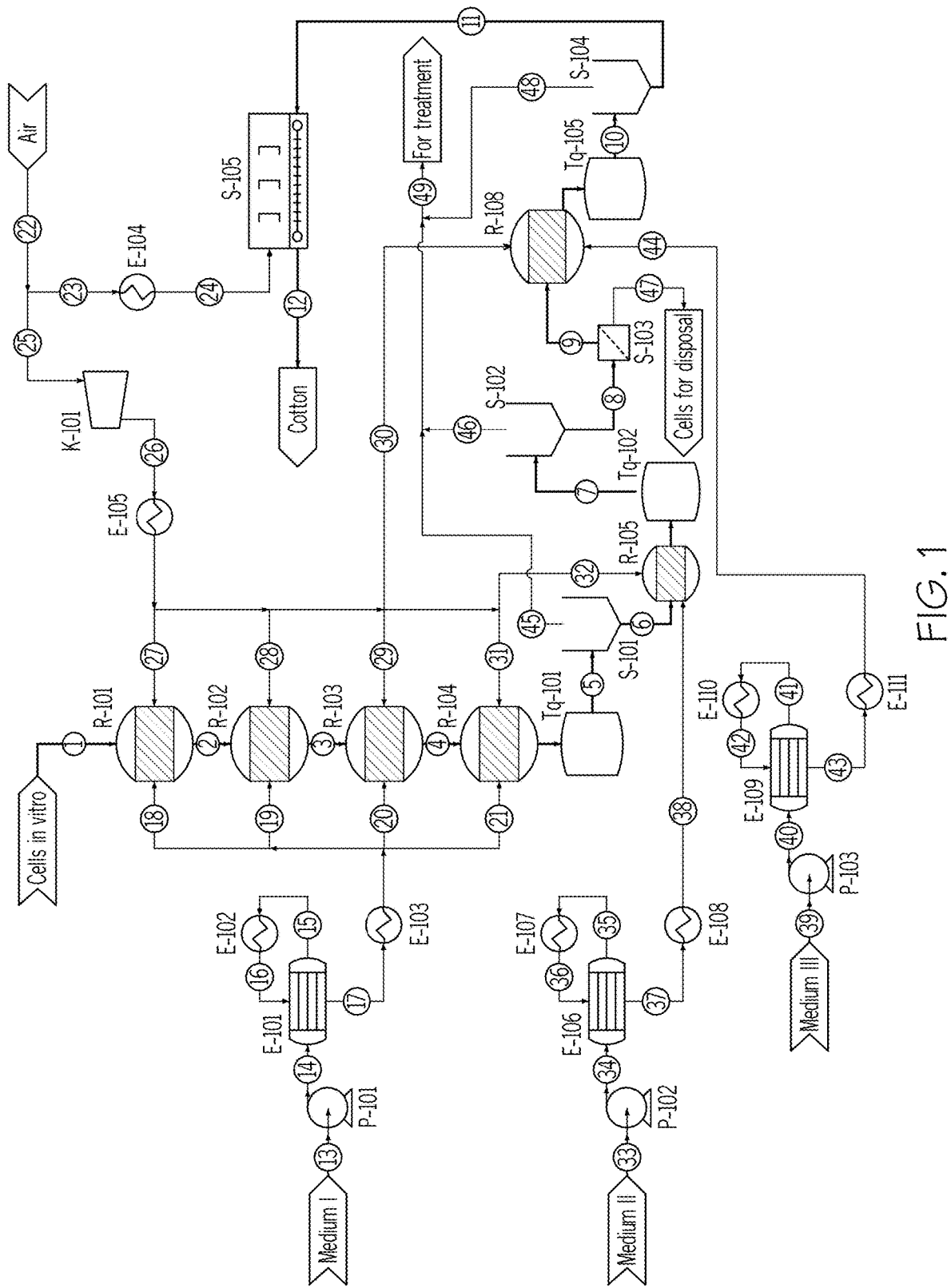
FIG. 1 shows a flowchart of the concept of a commercial scale process for the cotton fiber in vitro production.

While various embodiments of the invention have been shown and described herein, it will be apparent to those skilled in the art that such embodiments are provided by way of example only. Numerous variations, changes, and substitutions may occur to those skilled in the art without departing from the invention. It should be understood that various alternatives to the embodiments of the invention described herein may be employed.

Use of absolute or sequential terms, for example, "will," "will not," "shall," "shall not," "must," "must not," "first," "initially," "next," "subsequently," "before," "after," "lastly," and "finally" are not meant to limit scope of the present embodiments disclosed herein but as exemplary.

As used herein, the singular forms "a," "an," and "the" are intended to include the plural forms as well, unless the context clearly indicates otherwise. Furthermore, to the extent that the terms "including," "includes." "having," "has," "with," or variants thereof are used in either the detailed description and/or the claims, such terms are intended to be inclusive in a manner similar to the term "comprising."

Any systems, methods, software, compositions, and platforms described herein are modular and not limited to sequential steps. Accordingly, terms such as "first" and "second" do not necessarily imply priority, order of importance, or order of acts.

The terms "about" or "approximately," as used herein, mean within an acceptable error range for the particular value, which will depend in part on how the value is measured or determined, e.g., the limitations of the measurement system. For example, "about" can mean within 1 or more than 1 standard deviation, per the practice in the given value. Where particular values are described in the application and claims, unless otherwise stated, the term "about" should be assumed to mean an acceptable error range for the particular value.

The terms "increased" or "increase," as used herein, generally mean an increase by a statically significant amount. In some embodiments, the terms "increased" or "increase" mean an increase of at least 10% as compared to a reference level, for example, an increase of at least about 10%, at least about 20%, or at least about 30%, or at least about 40%, or at least about 50%, or at least about 60%, or at least about 70%, or at least about 80%, or at least about 90% or up to and including a 100% increase or any increase from 10% to 100% as compared to a reference level, standard, or control. Other examples of "increase" can include an increase of at least 2-fold, at least 5-fold, at least 10-fold, at least 20-fold, at least 50-fold, at least 100-fold, at least 1000-fold, or more as compared to a reference level.

The terms "decreased" or "decrease," as used herein, generally mean a decrease by a statistically significant amount. In some embodiments, "decreased" or "decrease" means a reduction by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease from 10% to 100% as compared to a reference level. In the context of a marker or symptom, by these terms is meant a statistically significant decrease in such level. The decrease can be, for example, at least 10%, at least 20%, at least 30%, at least 40% or more.

Whenever the term "at least," "greater than," or "greater than or equal to" precedes the first numerical value in a series of two or more numerical values, the term "at least," "greater than," or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "in vitro" can be used to describe an event that takes places contained in a container for holding laboratory reagent such that it is separated from the living biological source organism from which the material is obtained. In vitro assays can encompass cell-based assays in which cells alive or dead are employed. In vitro assays can also encompass a cell-free assay in which no intact cells are employed.

As used herein, the term "plant hormone(s)" is intended to include natural or synthetic hormone(s) and generally refers to naturally occurring (endogenous) substance(s) that promote, inhibit, or modify plant growth and development. The terms "plant hormone(s)" and "phytohormone(s)" are used interchangeably herein.

As used herein, the term "plant growth regulator(s)" generally refers to synthetic substance(s) that promote, inhibit, or modify plant growth and development.

As used herein, the term "auxin(s)" generally refers to natural or synthetic substance(s) that promote, inhibit, or modify plant growth and development, particularly elongation of plant cells. One of skill in the art will understand that the term "plant hormone(s) and (plant) growth regulator(s)" or "plant hormone(s) or (plant) growth regulator(s)," as used herein, is sufficiently broad to cover auxin(s).

As used herein, the term "solution" generally refers to a liquid with or without suspended substances. Non-limiting examples of a "solution" with suspended substances can include a suspension (such as a colloidal suspension, or a cell suspension), an emulsion, etc.

As used herein, the term "bioreactor" generally refers to a vessel capable of holding media for supporting plant cells in a desired physiological state, such as a fermenter, and also includes other devices such as hollow-fiber devices, perfusion devices, membrane devices, air lift reactors, capable of supporting plant cells in a desired physiological state.

An aspect of the present disclosure provides methods, kits, and compositions for preparing a plant cell composition, including any intermediate and final plant cell composition thereof.

Compositions

Provided herein, in some embodiments, are compositions related to a method for preparing a plant cell composition (such as described hereinbelow in the METHODS section or described anywhere else herein), and a method for producing engineered plant cells, for example, producing cotton or engineered cotton (such as any method described hereinbelow in the METHODS section or described anywhere else herein). In some embodiments, the compositions provided herein can be related to a starting material, any intermediate, an end-product, or a combination thereof of the method for preparing a plant cell composition or the method for producing engineered plant cells (e.g., producing cotton). In some embodiments, the composition provided herein can be a plant as described hereinbelow in the section entitled "Plant." In some embodiments, the composition provided herein can be a plant explant as described hereinbelow in the section entitled "Plant Explant." In some embodiments, the composition provided herein can be a plant callus as described hereinbelow in the section entitled "Plant Callus." In some embodiments, the composition provided herein can be a proliferating plant cell aggregate as described hereinbelow in the section entitled "Proliferating Cell Aggregate." In some embodiments, the composition provided herein can be a plant cell composition as described hereinbelow in the section entitled "Plant Cell Composition." In some embodiments, the composition provided herein can be cotton or engineered cotton as described hereinbelow in the section entitled "Engineered Cotton." In some embodiments, the composition described hereinbelow in the COMPOSITIONS section can be produced by utilizing a kit (or a medium of the kit, or a plurality of media of the kit) as described hereinbelow in the KITS section).

Plant

Some embodiments described herein are related to a plant. In some embodiments, the plant cell composition as described hereinbelow or described anywhere else herein can be derived from the plant. The plant can be a multicellular, predominantly photosynthetic eukaryote of the kingdom Plantae. In some cases, the plant can be a crop plant or a wild plant. The plant can have economic, social, and/or environmental value, such as food crops, fiber crops, oil crops, plants in the forestry or pulp and paper industries, feedstock for biofuel production, and/or ornamental plants. Non-limiting examples of the plant include a cotton plant, a saffron plant, a vanilla plant, a cocoa plant, a coffee plant, a rice plant, a pepper plant, or a stevia plant. Other examples of the plant can include maize, rice, wheat, barley, sorghum, millet, oats, rye, triticale, buckwheat, sweet corn, sugar cane, onions, tomatoes, strawberries, asparagus, pineapple, banana, coconut, lily, grass, peas, alfalfa, tomatillo, melon, chickpea, clover, kale, lentil, soybean, tobacco, potato, sweet potato, radish, cabbage, rape, apple, grape, sunflower, thale cress, canola, citrus (e.g., orange, mandarin, kumquat, lemon, lime, grapefruit, tangerine, tangelo, citron, or pomelo), bean, and lettuce.

In some embodiments, the plant described herein can have trichomes, or hair-like structures such as seed-hairs. Trichomes can be unicellular or multicellular. In some cases, the plant can yield other fibers similar to, instead of, or in addition to trichomes. In some embodiments, the trichomes can be relevant for textile or agricultural purposes. For example, the trichomes of some plants can be used to produce string, yarn, thread, or other textile components. Non-limiting examples of the plants having trichomes, seed-hairs, or other fibers can include akund floss, bagasse, bamboo, bombax cotton, coir, cotton, floss-silk tree, kapok, or milkweed floss.

In some embodiments, the plant described herein can have textile fibers. Examples of textile fibers can include bast fibers and leaf fibers. In some embodiments, the bast fiber can be a plant fiber collected from the phloem (inner bark) surrounding the stem of certain dicotyledonous plants. Non-limiting examples of the plants having bast fibers can include flax, hemp, Indian hemp, jute, tossa jute, white jute, kenaf, ramie, oselle, sunn, or urena. In some embodiments, the leaf fiber can be a fiber found in a vascular bundle of plant leaves. In some embodiments, the leaf fibers can be stronger than other types of fibers and may be used, for example, for cordage. Non-limiting examples of leaf fibers can include abaca, cantala, henequen, maguey, Mauritius hemp, phormium, or sisal.

In some embodiments, the plant described herein can comprise a pigment component. In some embodiments, the pigment component may be a natural component of the plant, such as an organic molecule that can be synthesized by the plant. In certain embodiments, the pigment component can be artificially increased or decreased (e.g., by modulating an expression level of one or more genes) in the plant. In various embodiments, the pigment component can be introduced to the plant, for example, by modifying the genome of the plant. Non-limiting examples of the pigment molecules can include anthocyanins, betalaines, crocin, carotenoids, anthraquinones, or naphthoquinones.

In some embodiments, the plant described herein can comprise a flavor molecule. In certain embodiments, the flavor molecule can be a natural component of the plant, such as an organic molecule that can be synthesized by the plant. In various embodiments, the flavor molecule can be artificially increased or decreased (e.g., by modulating an expression level of one or more genes) in the plant. In some embodiments, the flavor molecule can be introduced to the plant, for example, by modifying the genome of the plant. Non-limiting examples of plants that can comprise flavor molecules include vanillin, garlic, onion, coffee, or cocoa.

In some embodiments, the plant described herein can comprise a pungent food additive. In certain embodiments, the pungent food additive can be a natural component of a plant and can be artificially increased or decreased (e.g., by modulating an expression level of one or more genes) in the plant. In various embodiments, the pungent food additive can be introduced to the plant, for example, by modifying the genome of the plant. A non-limiting example of a pungent food additive can include capsaicin.

In some embodiments, the plant described herein can comprise a sweetening molecule. In some embodiments, the sweetening molecule can be a natural component of the plant such as an organic molecule that can be synthesized by the plant. In some embodiments, the sweetening molecule can be artificially increased or decreased (e.g., by modulating an expression level of one or more genes) in the plant. In some embodiments, the sweetening molecule can be introduced to the plant, for example, by modifying the genome of the plant. Non-limiting examples of sweetening molecules can include stevioside, glycyrrhizin, or thaumatin.

In some embodiments, the plant described herein can be a rosaceae, or a member of the rose family. Non-limiting examples of rosaceae can include plants yielding berries and plants yielding pomaceous fruit.

Plant Explant

Some embodiments described herein are related to a plant explant. In some embodiments, the plant cell composition as described herein can be derived from the plant explant. In some embodiments, the plant explant described herein can comprise one or more members selected from the group consisting of apical meristem, cotyledon, young leaf, hypocotyl, ovule, stem, mature leaf, flower, flower stalk, root, bulb, germinated seed, and cambial meristematic cell (CMC). In some embodiments, the plant explant described herein can comprise a CMC. In some embodiments, the plant explant described herein can comprise cambial meristematic cell (CMC) and one or more members selected from the group consisting of apical meristem, cotyledon, young leaf, hypocotyl, ovule, stem, mature leaf, flower, flower stalk, root, bulb, and germinated seed. The plant explant can be derived from a plant (such as any described hereinabove or described anywhere else herein). The plant explant can be a sample of a living plant, such as a sample removed from a living plant. In some cases where the plant explant is a sample removed from a living plant, the surface of the plant can be sterilized prior to removing the sample. In some cases, the explant can be sterilized after removal. The plant explant can be in a medium for preserving, maintaining, or culturing the explant. In some cases, the medium can be a sterile culture medium. In some embodiments, the medium can be a solid medium, a semi-solid medium, a gel medium, or a liquid medium. In some embodiments, the medium can be a callus induction medium, such as described hereinbelow in the K ITS section.

Plant Hormones or Growth Regulators

Some embodiments described herein are related to plant hormone(s) or/and growth regulator(s) (including auxins, gibberillins, etc.). In some embodiments, the plant cell composition as described hereinbelow or described anywhere else herein can be derived from plant hormones or/and growth regulators (including auxins, gibberillins, etc.). Plant hormones or/and growth regulators (including auxins, gibberillins, etc.) can be derived from naturally occurring sources, synthetically produced, or semi-synthetically produced, i.e. starting from naturally derived starting materials then synthetically modifying said materials. These modifications can be conducted using conventional methods as envisioned by a skilled worker. The following references include plant hormones and/or growth regulators (including auxins. gibberillins, etc.) for plant cell composition as described hereinbelow or described anywhere else herein: Gaspar et al., In Vitro Cell. Dev. Biol-Plant, 32, 272-289, October-December 1996 and Zhang et al., Journal of Integrative Agriculture, 2017, 16(8): 1720-1729; the contents of each of which (particularly, all the plant hormones and/or plant growth regulators) are incorporated by reference herein. In particular, one of skill in the art will understand that certain gibberillins are capable of facilitating plant cell elongation.

In some aspects, plant hormones or/and growth regulators are exemplified by those in Table A.

TABLE A

Exemplary plant hormones or plant growth regulators and exemplary applications in plant cell engineering.

| Name | Abbreviation | Callus induction | Multiplication | Fiber initiation/ elongation | Cell wall thickening | Other applications |
|---|---|---|---|---|---|---|
| indole acetic acid | IAA | Y | Y | Y | Y | |
| indole butyric acid | IBA | Y | Y | Y | Y | |
| 2,4-dichlorophenoxyacetic acid | 2,4 D | Y | Y | Y | Y | |
| naphthaleneacetic acid | NAA | Y | Y | Y | Y | |
| para-chlorophenoxyacetic acid | pCPA | Y | Y | Y | Y | |
| β-naphthoxyacetic acid | NOA | Y | Y | Y | Y | |
| 2-benzothiazole acetic acid | BTOA | Y | Y | Y | Y | |
| picloram | PIC | Y | Y | Y | Y | |
| 2,4,5,-trichlorophenoxyacetic acid | 2,4,5-T | Y | Y | Y | Y | |
| phenylacetic acid | PAA | Y | Y | Y | Y | |
| kinetin | KIN | Y | Y | Inhibitor | ND | |
| 6-benzylaminopurine | 6BA | Y | Y | Inhibitor | ND | |
| N6-(2-isopentenyl) adenine | 2iP | Y | Y | Inhibitor | ND | |
| zeatin | ZEA | Y | Y | Inhibitor | ND | |
| gibberellin A1 | GA1 | ND | ND | Y | ND | Control fiber strength, micronaire and maturation |
| gibberellic acid | GA3 | ND | ND | Y | ND | |
| gibberellin A4 | GA4 | ND | ND | Y | ND | |
| gibberellin A7 | GA7 | ND | ND | Y | ND | |
| ethylene | — | ND | ND | Y | ND | |
| brassinolide | BR | ND | ND | Y | Y | |
| jasmonic acid | JA | ND | ND | Y | ND | |

In Table A, "Y" indicates that the corresponding plant hormone or plant growth regulator in the row can be used for the application indicated in the column heading. In Table A, "Inhibitor" indicates that the corresponding plant hormone or plant growth regulator in the row can be used for inhibiting the activity indicated in the column heading. In Table A, "ND" indicates that effect(s) of the corresponding plant hormone or plant growth regulator for the application indicated in the column heading is not yet determined (at least to some extent).

Plant Callus

Some embodiments described herein are related to a plant callus. In some embodiments, the plant cell composition as described hereinbelow or described anywhere else herein can be derived from the plant callus. The plant callus can be a growing mass of plant parenchyma cells. In some cases, the mass of plant parenchyma cells can be unorganized. The plant callus can be collected from cells covering the wound of a plant or plant part, or from induction of a plant tissue sample (e.g., an explant). In some cases, induction of an explant can occur after surface sterilization and plating onto a medium in vitro (e.g., in a closed culture vessel such as a Petri dish). Induction can comprise supplementing the medium with plant growth regulators, such as auxins, cytokinins, or gibberellins to initiate callus formation. Induction can be performed at a temperature of, or of about, 20° C., 25° C., 28° C., 30° C., 35° C., or 40° C., or a range between any two foregoing values. In some embodiments, the plant callus described herein can be obtained using a medium described hereinbelow in the KITS section or described anywhere else herein. In some embodiments, the plant callus described herein can be obtained using a method described hereinbelow in the METHODS section or described anywhere else herein.

Proliferating Cell Aggregate

Some embodiments described herein are related to a proliferating cell aggregate. In some embodiments, the plant cell composition as described hereinbelow or described anywhere else herein can be derived from the proliferating cell aggregate. The proliferating cell aggregate can be an aggregate of plant cells that are proliferating. Proliferating cells in an aggregate can be attached or connected to each other, for example, via cell to cell interactions. The proliferating cell aggregate can be "a soft callus," which is friable, as opposed to "a hard callus," which is compact and brittle. Proliferating cells can be of one type (a homogenous aggregate) or of two or more types (a heterogeneous aggregate). The proliferating cell aggregate can be a mixed aggregate (e.g., where cell types are mixed together), a clustering aggregate (e.g., where cells of different types are tending toward different parts of the aggregate), or a separating aggregate (where cells of different types are pulling apart from each other). Cells of the proliferating cell aggregate can divide at a rate greater than a cell division rate of remaining cells in said plant callus. In some embodiments, cells of the proliferating cell aggregate can divide at a rate that can be at least 2, 3, 4, 5, 6, 7, 8, 9, 10, 20, 30, 40, or 50 times greater than a cell division rate of plant callus cells. In some embodiments, the plant callus described herein can be obtained using a medium described hereinbelow in the KITS section or described anywhere else herein. In some embodiments, the plant callus described herein can be obtained using a method described hereinbelow in the METHODS section or described anywhere else herein. In some embodiments, the cell culture medium can be a multiplication medium such as described hereinbelow in the KITS section.

Plant Cell Composition

Some embodiments described herein are related to a plant cell composition. In some embodiments, the plant cell composition as described hereinbelow or described anywhere else herein can be a cotton plant cell composition, a saffron cell composition, a vanilla cell composition, a cocoa cell composition, a coffee cell composition, a rice cell composition, a pepper cell composition, or a stevia cell composition. In some cases, cells of the plant cell composition can be configured to derive a pigment molecule, a food additive, or a fruit. In some cases, cells of the plant cell composition can be configured to derive a pigment molecule, a flavor molecule, a pungent food additive, a sweetening molecule, or a fruit. In some cases, cells of the plant cell composition can be configured to derive a trichome, a hair-like structure, or a fiber. In some cases, the plant cell composition can be a cotton cell composition. In some embodiments, the plant cell composition can be of another plant (such as any described in the immediately preceding paragraph). In some cases, the plant cell composition can comprise cells of two or more plants.

In some embodiments, the plant cell composition described herein can be a final product of a method for preparation of cell bank stocks provided herein. In some embodiments, the plant cell composition can be a composition of engineered cells, or a composition of cells. In some embodiments, the plant cell composition can be a cell bank stock. In some embodiments, the plant cell composition can comprise a plurality of plant cells obtained by growing the callus in a growth medium to produce a proliferating cell aggregate followed by culturing the proliferating cell aggregate.

In some embodiments, the plant cell composition described herein can be in a growth phase. In some embodiments, the growth phase can comprise cell division, cell enlargement, and/or cell differentiation. In some embodiments, the growth phase comprising cell division can be an exponential growth phase (e.g., dowaiting). In some embodiments, the exponential growth phase can occur as cells are mitotic. In some embodiments, during exponential growth, each generation of cells can be twice as numerous as the previous generation. In some embodiments, not all cells may survive in a given generation. In some embodiments, each generation of cells can be less than twice as numerous as the previous generation. In some embodiments, the exponential growth phase can be determined (e.g., quantified or identified) by a cell viability assay. In some embodiments, another aspect of the plant cell composition can be determined by a cell viability assay. In some embodiments, the cell viability assay can be an assay that can determine the ability of a cell to maintain or recover viability. In some embodiments, the cells of the plant cell composition can be assayed for their ability to divide or for active cell division. In some embodiments, the cell viability assay can be an ATP test, calcein AM, clonogenic assay, ethidium homodimer assay, Evans blue, fluorescein diacetate hydrolysis/propidium iodide staining (FDA/PI staining), flow cytometry, formazan-based assays (e.g., MTT or XTT), green fluorescent protein based assays, lactate dehydrogenase (LDH) based assays, methyl violet, neutral red uptake, propidium iodide, resazurin, trypan blue, or a TUNEL assay. In some embodiments, the cell viability assay can determine a cytoplasmic level of diphenol compounds in the plant cell composition.

In some embodiments, the plant cell composition described herein can comprise a plurality of plant cells. In some cases, the plant cell composition can comprise, or comprise about, $1 \times 10^2$, $5 \times 10^2$, $1 \times 10^3$, $5 \times 10^3$, $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, or $1 \times 10^9$ cells, or a range between any two foregoing values. In some cases, the plant cell composition can comprise at least, or at least about, $1 \times 10^2$, $5 \times 10^2$, $1 \times 10^3$, $5 \times 10^3$, $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, or $1 \times 10^9$ cells. In some cases, the plant cell composition can comprise at most, or at most about, $1 \times 10^2$, $5 \times 10^2$, $1 \times 10^3$, $5 \times 10^3$, $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, or $1 \times 10^9$ cells.

In some embodiments, cells of the plant cell composition described herein can have a cell, such as a maximum or minimum size (e.g., diameter, length, width, height, thickness, radius, or circumference). The cell size can be of, or of about, 10, 15, 20, 25, 30, 35, 40, 45, 50, 55, 60, 65, 70, 75, 80, 85, 90, 95, or 100 microns (μm, micrometers), or less. The cell size can be of, or of about, 10, 15, 20, 25, 30, 35, 40, 45, 50, 55, 60, 65, 70, 75, 80, 85, 90, 95, or 100 microns (μm, micrometers), or more. The cell size can be of, or of about, 10, 15, 20, 25, 30, 35, 40, 45, 50, 55, 60, 65, 70, 75, 80, 85, 90, 95, or 100 microns (μm, micrometers), or a range between any two foregoing values. In some embodiments, the cell size described herein is 100 μm or less. In some embodiments, the cell size described herein is 100 μm or less. In some embodiments, the cell size described herein is from 10 μm to 60 μm. In some embodiments, the cell size described herein is from 10 μm to 80 μm.

In some embodiments, a number of cells in the plant cell composition described herein can have a cell size (e.g., a minimum or maximum size). In some embodiments, the cell size can be determined using a microscope or other appropriate method. In some embodiments, at least 70% of the cells of the plant cell composition as described herein can have a cell size of at least about 10 μm, at least about 20 μm, at least about 30 μm, at least about 40 μm, at least about 50 μm, at least about 60 μm, at least about 80 μm, or at least about 100 μm. In some embodiments, at least 70% of cells can have a cell size of about 10 μm or less, about 20 μm or less, about 50 μm or less, about 60 μm or less, about 70 μm or less, about 80 μm or less, about 90 μm or less, or about 100 μm or less. In some embodiments, at least 70% of cells of the plant cell composition as described herein can have a cell size from about 10 μm to about 80 μm. In some embodiments, at least 70% of cells of the plant cell composition as described herein can have a cell size from about 10 μm to about 60 μm. In some embodiments, at least 80% of the cells of the plant cell composition as described herein can have a cell size of at least about 10 μm, at least about 20 μm, at least about 30 μm, at least about 40 μm, at least about 50 μm, at least about 60 μm, at least about 80 μm, or at least about 100 μm. In some embodiments, at least 80% of cells of the plant cell composition as described herein can have a cell size of about 10 μm or less, about 20 μm or less, about 50 μm or less, about 60 μm or less, about 70 μm or less, about 80 μm or less, about 90 μm or less, or about 100 μm or less. In some embodiments, at least 80% of the cells of the plant cell composition described herein can have a cell size from about 10 μm to about 80 μm. In some embodiments, at least 80% of the cells of the plant cell composition as described herein can have a cell size from about 10 μm to about 60 μm. In some embodiments, at least 90% of the cells of the plant cell composition as described herein can have a cell size of at least about 10 μm, at least about 20 μm, at least about 30 μm, at least about 40 μm, at least about 50 μm, at least about 60 μm, at least about 80 μm, or at least about 100 μm. In some embodiments, at least 90% of the cells of the plant cell composition as described herein can have a cell size of about 10 μm or less, about 20 μm or less, about 50 μm or less, about 60 μm or less, about 70 μm or less, about 80 μm or less, about 90 μm or less, or about 100 μm or less. In some embodiments, at least 90% of the cells of the plant cell composition as described herein can have a cell size from about 10 μm to about 80 μm. In some embodiments, at least 90% of the cells of the plant cell composition as described herein can have a cell size from about 10 pam to about 60 μm. The term "about," as used herein when referring to the cell size, generally allows for a degree of variability in the cell size (e.g., ±1 μm, ±2 μm, ±3 μm, or ±5 μm).

In some embodiments, cells of the plant cell composition described herein have (for example, can be measured, calculated, and/or expressed to have) a distribution of cell size. The distribution of cell size can be expressed as a function of a minimum cell size and a maximum cell size in the composition. In some embodiments, the distribution of cell size can be expressed as a mean cell size and a standard deviation of cell size. In some embodiments, the distribution of cell size can have a width. In some embodiments, the width of the distribution of cell size can be expressed as the difference between the maximum cell size and the minimum cell size, a standard deviation of cell size, 2 standard deviations of cell size, or 4 standard deviations of cell size. In some embodiments, the distribution of cell size can be narrower than another distribution of cell size (i.e., having a smaller distribution width than another plant cell composition) or wider than another distribution of cell size (i.e., having a larger distribution width than another plant cell composition). In some embodiments, the plant cell composition can have a distribution of cell size that is narrower than that of a proliferating cell aggregate. In some embodiments, the plant cell composition can have a distribution of cell size than is not more than 10% of, not more than 20% of, not more than 30% of, not more than 40% of, not more than 50% of, not more than 60% of, not more than 70% of, or not more than 80% of that of a proliferating cell aggregate. In some embodiments, the plant cell composition described herein has a distribution of cell size that is narrower than the proliferating cell aggregate, from which the plant cell composition is derived. In such embodiments, the distribution of cell size of the plant cell composition can be about 5%, about 10%, about 15%, or about 20% narrower than the proliferating cell aggregate.

In some embodiments, a cell in a plant cell composition described herein can have a vacuole, which can be a membrane bound organelle. In some embodiments, the vacuole of the plant cell can be an essentially enclosed compartment filled with water as well as inorganic and/or organic molecules. In some embodiments, the vacuole of the plant cell can be surrounded by a vacuolar membrane called a tonoplast, which can separate the vacuolar contents from the cytoplasm. In some embodiments, the vacuole of the plant cell can comprise contents that are different than those found in the cytoplasm, which can include but are not limited to materials that might be harmful or a threat to a cell, or materials that may need transported from one part of a cell to another. In some embodiments, the vacuole of the plant cell can be filled with cell sap. In some embodiments, the vacuole of the plant cell can have a size that is less than the total size of the plant cell. In some embodiments, the vacuole size can be determined, for example, using a microscope. In some embodiments, the vacuole size can be measured and/or expressed as a percentage of the total volume of the cell. In some embodiments, cell volume can be measured directly or estimated, for example, using microscopy and/or mathematical techniques. In some embodiments, the cell of the plant cell composition as described herein can comprise a vacuole that can occupy 20% or more, 30% or more, 40% or more, 50% or more, 60% or more, 70% or more, or 80% or more by volume of the plant cell. In some embodiments, the cell of the plant cell composition as described herein can comprise a vacuole that can occupy not more than 20%, not more than 30%, not more than 40%, not more than 50%, not more than 60%, not more than 70%, or not more than 80% by volume of the plant cell. In some embodiments, the cell of the plant cell composition as described herein can comprise a vacuole than can occupy from 20% to 80%, from 30% to 80%, from 40% to 80%, from 50% to 80%, from 60% to 80%, from 70% to 80%, from 20% to 70%, from 30% to 70%, from 40% to 70%, from 50% to 70%, from 60% to 70%, from 20% to 60%, from 30% to 60%, from 40% to 60%, from 50% to 60%, from 20% to 50%, from 30% to 50%, from 40% to 50%, from 20% to 40%, from 30% to 40%, or from 20% to 30% by volume of the plant cell.

In some embodiments, no more than 10% of cells of the plant cell composition as described herein can comprise a vacuole that can occupy 20% or more, 30% or more, 40% or more, 50% or more, 60% or more, 70% or more, or 80% or more by volume of the plant cell. In some embodiments, no more than 10% of the cells of the plant cell composition as described herein can comprise a vacuole that can occupy not more than 20%, not more than 30%, not more than 40%, not more than 50%, not more than 60%, not more than 70%, or not more than 80% by volume of the plant cell. In some embodiments, no more than 20% of the cells of the plant cell composition as described herein can comprise a vacuole that can occupy 20% or more, 30% or more, 40% or more, 50% or more, 60% or more, 70% or more, or 80% or more by volume of the plant cell. In some embodiments, no more than 20% of the cells of the plant cell composition as described herein can comprise a vacuole that can occupy not more than 20%, not more than 30%, not more than 40%, not more than 50%, not more than 60%, not more than 70%, or not more than 80% by volume of the plant cell. In some embodiments, no more than 30% of the cells of the plant cell composition as described herein can comprise a vacuole that can occupy 20% or more, 30% or more, 40% or more, 50% or more, 60% or more, 70% or more, or 80% or more by volume of the plant cell. In some embodiments, no more than 30% of the cells of the plant cell composition as described herein can comprise a vacuole that can occupy not more than 20%, not more than 30%, not more than 40%, not more than 50%, not more than 60%, not more than 70%, or not more than 80% by volume of the plant cell. In some embodiments, no more than 40% of the cells of the plant cell composition as described herein can comprise a vacuole that can occupy 20% or more, 30% or more, 40% or more, 50% or more, 60% or more, 70% or more, or 80% or more by volume of the plant cell. In some embodiments, no more than 40% of the cells of the plant cell composition as described herein can comprise a vacuole that can occupy not more than 20%, not more than 30%, not more than 40%, not more than 50%, not more than 60%, not more than 70%, or not more than 80% by volume of the plant cell. In some embodiments, no more than 50% of the cells of the plant cell composition as described herein can comprise a vacuole that can occupy 20% or more, 30% or more, 40% or more, 50% or more, 60% or more, 70% or more, or 80% or more by volume of the plant cell. In some embodiments, no more than 50% of cells of the plant cell composition as described herein can comprise a vacuole that can occupy not more than 20%, not more than 30%, not more than 40%, not more than 50%, not more than 60%, not more than 70%, or not more than 80% by volume of the plant cell.

In some embodiments, the vacuole size of a vacuole in the cell of the plant cell composition as described herein can be measured as a dimension (e.g., a length or a width). In some embodiments, the cell in the plant cell composition as described herein can have a dimension of at least 1 µm, at least 2 µm, at least 3 µm, at least 4 µm, at least 5 µm, at least 6 µm, at least 7 µm, at least 8 µm, at least 9 µm, or at least 10 µm. In some embodiments, the vacuole size of the vacuole in the cell of the plant cell composition as described herein can have a dimension of not more than 1 µm, not more than 2 µm, not more than 3 µm, not more than 4 µm, not more than 5 µm, not more than 6 µm, not more than 7 µm, not more than 8 µm, not more than 9 µm, or not more than 10 µm. In some embodiments, the vacuole size of the vacuole in the cell of the plant cell composition as described herein can have a dimension of about 1 µm, about 2 µm, about 3 µm, about 4 µm, about 5 µm, about 6 µm, about 7 µm, about 8 µm, about 9 µm, about 10 µm, or a range between any two foregoing values. In some embodiments, the vacuole size of the vacuole in the cell of the plant cell composition as described herein can have a dimension of 3 µm to 8 µm. In some embodiments, at least 70% of the cells in the plant cell composition as described herein can have a vacuole having a dimension of about 1 µm, about 2 µm, about 3 µm, about 4 µm, about 5 µm, about 6 µm, about 7 µm, about 8 µm, about 9 µm, about 10 µm, or a range between any two foregoing values. In some embodiments, at least 70% of the cells in the plant cell composition as described herein can have a vacuole having a dimension of 3 µm to 8 µm. In some embodiments, at least 80% of the cells in the plant cell composition as described herein can have a vacuole having a dimension of about 1 µm, about 2 µm, about 3 µm, about 4 µm, about 5 µm, about 6 µm, about 7 µm, about 8 µm, about 9 µm, about 10 µm, or a range between any two foregoing values. In some embodiments, at least 80% of the cells in the plant cell composition as described herein can have a vacuole having a dimension of 3 µm to 8 µm.

In some embodiments, the vacuole size of the vacuoles of the cells in the plant cell composition described herein has (for example, can be measured, calculated, and/or expressed to have) a distribution of vacuole size. In some embodiments, the distribution of vacuole size can be expressed as a function of a minimum vacuole size and a maximum vacuole size in the composition. In some embodiments, the distribution of vacuole size can be expressed as a mean vacuole size and a standard deviation of vacuole size. In some embodiments, the distribution of vacuole size can have a width. In some embodiments, the width of the distribution of vacuole size of the cells in the plant cell composition described herein can be expressed as the difference between the maximum vacuole size and the minimum vacuole size, a standard deviation of vacuole size, 2 standard deviations of vacuole size, or 4 standard deviations of vacuole size. In some embodiments, the distribution of vacuole size can be narrower than another distribution of vacuole size (i.e., having a smaller distribution width than another plant cell composition) or wider than another distribution of vacuole size (i.e., having a larger distribution width than another plant cell composition). In some embodiments, the plant cell composition as described herein can have a distribution of vacuole size narrower than that of a proliferating cell aggregate. In some embodiments, the plant cell composition as described herein can have a distribution of vacuole size than is not more than 10% of, not more than 20% of, not more than 30% of, not more than 40% of, not more than 50% of, not more than 60% of, not more than 70% of, or not more than 80% of that of a proliferating cell aggregate. In some embodiments, the plant cell composition described herein has a distribution of cell vacuole size that is narrower than said proliferating cell aggregate, from which the plant cell composition is derived. In such embodiments, the distribution of cell vacuole size of the plant cell composition can be about 5%, about 10%, about 15%, or about 20% narrower than the proliferating cell aggregate.

In some embodiments, the cells of a plant cell composition described herein can have in increased cytoplasmic optical density compared with the optical density of a corresponding non dividing cell. In some embodiments, the optical density can be measured, for example, by using a spectrophotometer. In some embodiments, at least 50%, at least 60%, at least 70%, at least 80%, or at least 90% of the cells in the plant cell composition can have a cytoplasmic optical density greater than the cytoplasmic optical density of the corresponding non-dividing cell. In some embodiments, at least 80% of the cells of the plant cell composition described herein can have a cytoplasmic optical density greater than a cytoplasmic optical density of a corresponding non-dividing cell. In some embodiments, at least 90% of the cells of the plant cell composition described herein can have a cytoplasmic optical density greater than the cytoplasmic optical density of a corresponding non-dividing cell. In some compositions, the cells in the plant cell composition can have a cytoplasmic optical density that is at least 10% greater than, at least 50% greater than, at least 100% greater than, at least 200% greater than, at least 500% greater than, or at least 1000% greater than the cytoplasmic optical density of the corresponding non-dividing cell.

In some embodiments, the cytoplasmic optical density of the cell in the plant cell composition described herein can be determined using a spectrophotometer by measuring the amount of light of a given wavelength that can be transmitted through the cell of the plant cell composition or a suspension of cells of the plant cell composition. In some embodiments, the cytoplasmic optical density of the cell of the plant cell composition can be determined by a spectrophotometer at a wavelength of about 180 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, or a range between any two foregoing values. In some embodiments, the cytoplasmic optical density of the cell of the plant cell composition can be determined by a spectrophotometer at a wavelength of from 180 nm to 800 nm. In some embodiments, the cytoplasmic optical density of the cell of the plant cell composition can be determined by a spectrophotometer at a wavelength of from 200 nm to 700 nm. In some embodiments, the cytoplasmic optical density of the cell of the plant cell composition can be determined using a spectrophotometer to be at least 0.4, at least 0.45, at least 0.5, at least 0.55, or at least 0.6. In some embodiments, the cytoplasmic optical density of the cell of the plant cell composition can be determined using a spectrophotometer to be not more than 0.4, not more than 0.45, not more than 0.5, not more than 0.55, or not more than 0.6. In some embodiments, the cytoplasmic optical density of the cell of the plant cell composition can be determined using a spectrophotometer to be about 0.4, about 0.45, about 0.5, about 0.55, about 0.6, or a range between any two foregoing values. In some embodiments, the cytoplasmic optical density of the cell of the plant cell composition can be from 0.4 to 0.6. In some embodiments, the cytoplasmic optical density of the cells in the plant cell composition described herein has (for example, can be measured, calculated, and/or expressed to have) a distribution of cytoplasmic optical density. In some embodiments, the distribution of cytoplasmic optical density of the cells in the plant cell composition can be expressed as a function of a minimum cytoplasmic optical density and a maximum cytoplasmic optical density of the cytoplasm of cells in the composition. In some embodiments, the distribution of cytoplasmic optical density of the cells in the plant cell composition can be expressed as a mean cytoplasmic optical density and a standard deviation of cytoplasmic optical density. In some embodiments, the distribution of cytoplasmic optical density of the cells in the plant cell composition described herein can have a width. In some embodiments, the width of the cytoplasmic optical density of the cells in the plant cell composition can be expressed as the difference between the maximum cytoplasmic optical density and the minimum cytoplasmic optical density, a standard deviation of cytoplasmic optical density, 2 standard deviations of cytoplasmic optical density, or 4 standard deviations of cytoplasmic optical density. In some embodiments, the distribution of cytoplasmic optical density of the cells in the plant cell composition can be narrower than another distribution of cytoplasmic optical density (i.e., having a smaller distribution width than another plant cell composition) or wider than another distribution of cytoplasmic optical density (i.e., having a larger distribution width than another plant cell composition). In some embodiments, the cells of the plant cell composition can have a distribution of cytoplasmic optical density narrower than the distribution of cytoplasmic optical density of a proliferating cell aggregate. In some embodiments, the cells of the plant cell composition can have a distribution of cytoplasmic optical density than is not more than 10% of, not more than 20% of, not more than 30% of, not more than 40% of, not more than 50% of, not more than 60% of, not more than 70% of, or not more than 80% of that of a proliferating cell aggregate. In some embodiments, the plant cell composition described herein has a distribution of cell cytoplasmic optical density that is narrower than the proliferating cell aggregate, from which the plant cell composition is derived. In such embodiments, the distribution of cell cytoplasmic optical density of the plant cell composition can be about 5%, about 10%, about 15%, or about 20% narrower than the proliferating cell aggregate.

In some embodiments, the cells of a plant cell composition described herein can comprise at least two of: a cell size as described above, an optical density as described above, and a vacuole dimension as described above. In some embodiments, the cells of a plant cell composition described herein can comprise a cell size as described herein and an optical density as described herein. In some embodiments, the cells of a plant cell composition described herein can comprise a cell size as described herein and a vacuole dimension as described herein. In some embodiments, the cells of a plant cell composition described herein can comprise an optical density as described herein and a vacuole dimension as described above. In some embodiments, the cells of a plant cell composition described herein can comprise all of a cell size as described herein, an optical density as described herein, and a vacuole dimension as described herein.

In some embodiments, for example, the plant cell composition can comprise cells such that at least 70% of the cells can have a cell size of 100 μm or less and at least 70% of the cells can have a cytoplasmic optical density greater than a cytoplasmic optical density of a corresponding non-dividing cell. In some embodiments, a plant cell composition can comprise cells such that at least 70% of the cells can have a cytoplasmic optical density greater than a cytoplasmic optical density of a corresponding non-dividing cell and at least 70% of the cells have a vacuole having a dimension of from 3 μm to 8 μm. As another example, a plant cell composition can comprise cells such that at least 70% of the cells have a cell size of 100 μm or less and at least 70% of the cells have a vacuole having a dimension of form 3 μm to 8 μm. As yet another example, a plant cell composition can comprise cells such that at least 70% of the cells can have a cell size of 100 μm or more, at least 70% of the cells can have a cytoplasmic optical density greater than a cytoplasmic optical density of a corresponding non-dividing cell and at least 70% of the cells have a vacuole having a dimension of from 3 μm to 8 μm. In addition to these illustrative examples, in some embodiments, plant cell compositions described herein can comprise other combinations consistent with cell size, cytoplasmic optical density, and vacuole dimensions described herein.

Some embodiments of the plant cell composition as described hereinabove in this section entitled "Plant Cell Composition" are a cotton cell composition.

Engineered Cotton

Disclosed herein, in some embodiments, are cotton (or engineered cotton), cotton fibers (or engineered cotton fibers), compositions comprising cotton (or engineered cotton), and compositions comprising cotton fibers (or engineered cotton fibers). Some embodiments of the cotton (or engineered cotton), as described hereinbelow in this section entitled "Engineered Cotton," can be produced by using a method provided hereinbelow in the METHODS section or anywhere else herein (such as the methods for producing cotton).

In some embodiments, the cotton (or engineered cotton) described herein can be derived from a *Gossypium* species. The *Gossypium* species can be selected from the group consisting of *G. arboreum, G. anomalum, G. armourianum, G. klotzchianum*, and *G. raimondii*. The cotton (or engineered cotton) can be derived from a *Gossypium* species selected from the group consisting of *G. hirsutum, G. arboreum, G. barbadense, G. anomalum, G. armourianum, G. klotzchianum*, and *G. raimondii*. The cotton (or engineered cotton) can be *Gossypium hirsutum, Gossypium barbadense, Gossypium arboretum, Gossypium herbaceum*, or another species of cotton.

In some embodiments, the cotton (or engineered cotton) described herein can have a dry mass of at least 10 grams per liter (g/L) fresh weight (FW) (e.g., grams of dry mass obtained per liter of fresh weight cotton cells). In some embodiments, the dry mass of the cotton (or engineered cotton) can be at least 50 grams per liter (g/L) fresh weight (FW). In some embodiments, the dry mass of the cotton (or engineered cotton) can be at least 100 grams per liter (g/L) fresh weight (FW). In some embodiments, the dry mass of the cotton (or engineered cotton) can be from 50 grams per liter (g/L) fresh weight (FW) to 500 g/L (FW). In some embodiments, the dry mass of the cotton (or engineered cotton) can be from 100 grams per liter (g/L) fresh weight (FW) to 500 g/L (FW). In some embodiments, the dry mass of the cotton (or engineered cotton) can be from 100 grams per liter (g/L) fresh weight (LW) to 300 g/L (FW). In some embodiments, the dry mass of the cotton (or engineered cotton) can have a dry mass of about 50 grams per liter (g/L) fresh weight (FW), about 100 g/L FW, about 200 g/L LW, about 300 g/L FW, about 400 g/L FW, about 500 g/L FW, about 600 g/L FW, about 700 g/L FW, about 800 g/L FW, about 900 g/L FW, or about 1000 g/L FW, or a range between any of the foregoing values. In some embodiments, the dry mass of the cotton (or engineered cotton) can have a dry mass of at least 50 grams per liter (g/L) fresh weight (FW), at least 100 g/L FW, at least 200 g/L FW, at least 300 g/L LW, at least 400 g/L FW, at least 500 g/L FW, at least 600 g/L FW, at least 700 g/L FW, at least 800 g/L FW, at least 900 g/L FW, or at least 1000 g/L FW, or a range between any of the foregoing values. In some embodiments, the cotton (or engineered cotton) described herein can have a dry mass of at least 50 milligrams (mg). In some embodiments, the cotton can have a dry mass of at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, or at least 1000 mg. In some embodiments, the cotton can have a dry mass of at least 1 gram (g), at least 5 g, at least 10 g, at least 50 g, at least 100 g, at least 500 g, at least 1 kg, at least 5 kg, at least 10 kg, at least 50 kg, or at least 100 kg.

In some embodiments, the cotton (or engineered cotton) described herein can comprise, or comprise about, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, or a range between any two foregoing, by dry weight of a trash content (TC). In some embodiments, the cotton (or engineered cotton) described herein can comprise at most, or comprise at most about, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by dry weight of a trash content. In some embodiments, the cotton (or engineered cotton) described herein can comprise at least, or comprise at least about, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by dry weight of a trash content. In some embodiments, the cotton (or engineered cotton) can comprise at most 10% by dry weight of a trash content. In some embodiments, the cotton (or engineered cotton) can comprise at most 8% by dry weight of a trash content. In some embodiments, the cotton (or engineered cotton) can comprise at most 5% by dry weight of a trash content. In some embodiments, the cotton (or engineered cotton) can comprise at most 2% by dry weight of a trash content. In some embodiments, the cotton can comprise at most 1% by dry weight of a trash content. In some embodiments, the cotton can comprise at most 0.5% by dry weight of a trash content. In some embodiments, the cotton can comprise at most 0.2% by dry weight of a trash content. In some embodiments, the cotton can comprise at most 0.1% by dry weight of a trash content. In some embodiments, the trash content can be a non-lint substance (such as non-cotton substance and cottons with convolutions, strings, conjoint defects, motes, or broken seeds). The "trash content" of a cotton sample can be measured by a Premier G-Trash Tester.

In some embodiments, the cotton (or engineered cotton) described herein comprises cotton fibers. A cotton fiber of the cotton (or engineered cotton) can be an elongated cotton cell. In some embodiments, the cotton (or engineered cotton) described herein can comprise at least 70%, at least 75%, at least 80%, at least 85%, at least 90%, at least 95%, or at least 99% by dry weight cotton fibers. In some embodiments, the cotton (or engineered cotton) can comprise at least 90% by dry weight cotton fibers.

In some embodiments, the cotton fibers of the cotton (or engineered cotton) as described herein can comprise, by dry weight, a maximum threshold of a short fiber content (SFC). In some embodiments, the cotton fibers of the cotton (or engineered cotton) as described herein can comprise, or comprise about, 1%, 5%, 10%, 15%, 20%, 25%, or 30%, or a range between any two forgoing, by dry weight, a short fiber content (SFC). In some embodiments, the cotton fibers of the cotton (or engineered cotton) as described herein can comprise at most 30%, at most 25%, at most 20%, at most 15%, at most 10%, at most 5%, or at most 1%, by dry weight, a short fiber content (SFC). In some embodiments, the cotton fibers of the cotton (or engineered cotton) as described herein can comprise at most 10% by dry weight a short fiber content (SFC). In some embodiments, the cotton fibers of the cotton (or engineered cotton) as described herein can comprise at least 1%, at least 5%, at least 10%, at least 15%, at least 20%, at least 25%, or at least 30% by dry weight a short fiber content (SFC). In some embodiments, cotton fibers of the short fiber contents have a length no more than a pre-determined length (such as 0.5 inch, or any length from 2.2 to 3.0 centimeter (cm)).

In some embodiments, the cotton fibers of the cotton (or engineered cotton) as described herein (or the plurality of elongated cotton cells as obtained using a method described hereinbelow in the METHODS section or described anywhere else) can have an average fiber length of, or of about, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 centimeters (cm), or a range between any two foregoing values. In some embodiments, the cotton fibers of the cotton (or engineered cotton) (or the plurality of elongated cotton cells as obtained using a method described hereinbelow in the METHODS section or described anywhere else) have an average fiber length of from 1.1 centimeter (cm) to 4.0 cm.

In some embodiments, the cotton fibers of the cotton (or engineered cotton) as described herein can have a length uniformity. The length uniformity can be an indicator of how similar the lengths of cotton fibers are in a cotton composition. In some embodiments, the cotton fibers can have a length uniformity of, or of about, 60%, 65%, 70%, 75%, 80%, 85%, 90%, 95%, or 99%, or a range between any two foregoing values. In some embodiments, the cotton fibers can have a length uniformity of at least 70%. In some embodiments, the cotton fibers can have a length uniformity of at least 50%, at least 55%, at least 60%, at least 65%, at least 70%, at least 75%, at least 80%, at least 85%, or at least 90%. In some embodiments, the cotton fibers can have a length uniformity of at most 50%, at most 55%, at most 60%, at most 65%, at most 70%, at most 75%, at most 80%, at most 85%, or at most 90%.

In some embodiments, the cotton fibers of the cotton (or engineered cotton) as described herein can comprise a secondary wall. The secondary wall of the cotton fibers described herein can have an average thickness. The average thickness of the secondary wall of the cotton fibers can be of, or of about, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5, 4.6, 4.7, 4.8, 4.9, 5.0, 5.5, or 6.0 micron (μm), or a range between any two foregoing values. The average thickness of the secondary wall of the cotton fibers can be at most, or at most about, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5, 4.6, 4.7, 4.8, 4.9, 5.0, 5.5, or 6.0 micron (μm). The average thickness of the secondary wall of the cotton fibers can be at least, or at least about, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5, 4.6, 4.7, 4.8, 4.9, 5.0, 5.5, or 6.0 micron (μm). In some embodiments, the cotton fibers described herein can have an average thickness of a secondary wall of at least 4 μm.

In some embodiments, the cotton fibers of the cotton (or engineered cotton) as described herein can comprise a threshold amount of cellulose by dry weight. In some embodiments, the cotton fibers can comprise, or comprise about, by dry weight, 80%, 81%, 82%, 83%, 84%, 85%, 86%, 87%, 88%, 89%, 90%, 91%, 92%, 93%, 94%, 95%, 96%, 97%, 98%, or 99% cellulose, or a range between any two foregoing values. In some embodiments, the cotton fibers can comprise at least, or comprise at least about, by dry weight, 80%, 81%, 82%, 83%, 84%, 85%, 86%, 87%, 88%, 89%, 90%, 91%, 92%, 93%, 94%, 95%, 96%, 97%, 98%, or 99% cellulose. In some embodiments, the cotton fibers can comprise at most, or comprise at most about, by dry weight, 80%, 81%, 82%, 83%, 84%, 85%, 86%, 87%, 88%, 89%, 90%, 91%, 92%, 93%, 94%, 95%, 96%, 97%, 98%, or 99% cellulose. In some embodiments, the cotton fibers can comprise, by dry weight, from 88% to 96% cellulose. In some embodiments, the cotton fibers of the cotton (or engineered cotton) as described herein can comprise a threshold amount of protein by dry weight. In some embodiments, the cotton fibers can comprise, or comprise about, by dry weight, 0.7%, 0.8%, 0.9%, 1.0%, 1.2%, 1.3%, 1.4%, 1.5%, 1.6%, 1.7%, 1.8%, 1.9%, 2.0%, 2.1%, 2.2%, 2.3%, 2.4%, 2.5% protein, or a range between any two foregoing values. In some embodiments, the cotton fibers can comprise at least, or comprise at least about, by dry weight, 0.7%, 0.8%, 0.9%, 1.0%, 1.2%, 1.3%, 1.4%, 1.5%, 1.6%, 1.7%, 1.8%, 1.9%, 2.0%, 2.1%, 2.2%, 2.3%, 2.4%, 2.5% protein. In some embodiments, the cotton fibers can comprise at most, or comprise at most about, by dry weight, 0.7%, 0.8%, 0.9%, 1.0%, 1.2%, 1.3%, 1.4%, 1.5%, 1.6%, 1.7%, 1.8%, 1.9%, 2.0%, 2.1%, 2.2%, 2.3%, 2.4%, 2.5% protein. In some embodiments, the cotton fiber can comprise, by dry weight, from 1.1% to 1.9% protein.

In some embodiments, the cotton fibers of the cotton (or engineered cotton) as described herein can comprise a threshold amount of pectic substance by dry weight. In some embodiments, the cotton fibers can comprise, or comprise about, by dry weight, 0.5%, 0.6%, 0.7%, 0.8%, 0.9%, 1.0%, 1.1%, 1.2%, 1.3%, 1.4%, 1.5%, 1.6%, 1.7%, or 1.8% pectic substance, or a range between any two foregoing values. In some embodiments, the cotton fibers can comprise at least, or comprise at least about, by dry weight, 0.5%, 0.6%, 0.7%, 0.8%, 0.9%, 1.0%, 1.1%, 1.2%, 1.3%, 1.4%, 1.5%, 1.6%, 1.7%, or 1.8% pectic substance. In some embodiments, the cotton fibers can comprise at most, or comprise at most about, by dry weight, 0.5%, 0.6%, 0.7%, 0.8%, 0.9%, 1.0%, 1.1%, 1.2%, 1.3%, 1.4%, 1.5%, 1.6%, 1.7%, or 1.8% pectic substance. In some embodiments, the cotton fiber can comprise, by dry weight, from 0.7% to 1.2% pectic substance.

In some embodiments, the cotton fibers of the cotton (or engineered cotton) as described herein can comprise a threshold amount of ash by dry weight. In some embodiments, the cotton fibers can comprise, or comprise about, by dry weight, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0% ash, or a range between any two foregoing values. In some embodiments, the cotton fibers can comprise at least, or comprise at least about, by dry weight, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0% ash. In some embodiments, the cotton fibers can comprise at most, or comprise at most about, by dry weight, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0% ash. In some embodiments, the cotton fibers can comprise, by dry weight, from 0.7% to 1.6% ash.

In some embodiments, the cotton fibers of the cotton (or engineered cotton) as described herein can comprise a threshold amount of wax by dry weight. In some embodiments, the cotton fibers can comprise, or comprise about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% wax, or a range between any two foregoing values. In some embodiments, the cotton fibers can comprise at least, or comprise at least about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% wax. In some embodiments, the cotton fibers can comprise at most, or comprise at most about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% wax. In some embodiments, the cotton fibers can comprise, by dry weight, from 0.4% to 1.1% wax.

In some embodiments, the cotton fibers of the cotton (or engineered cotton) as described herein can comprise a threshold amount of sugar by dry weight. In some embodiments, the cotton fibers can comprise, or comprise about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% sugar, or a range between any two foregoing values. In some embodiments, the cotton fibers can comprise at least, or comprise at least about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% sugar. In some embodiments, the cotton fibers can comprise at most, or comprise at most about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, 1.5% sugar. In some embodiments, the cotton fibers can comprise, by dry weight, from 0.1% to 1.1% sugar.

In some embodiments, the cotton fibers of the cotton (or engineered cotton) as described herein can comprise a threshold amount of organic acid by dry weight. In some embodiments, the cotton fibers can comprise, or comprise about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% organic acid, or a range between any two foregoing values. In some embodiments, the cotton fibers can comprise at least, or comprise at least about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% organic acid. In some embodiments, the cotton fibers can comprise at most, or comprise at most about, by dry weight, 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% organic acid. In some embodiments, the cotton fibers can comprise, by dry weight, from 0.5% to 1.0% organic acid.

In some embodiments, the cotton fibers of the cotton (or engineered cotton) as described herein can comprise, by dry weight, 88% to 96% cellulose, 1.1% to 1.9% protein, and 0.7% to 1.2% pectic substance. In some embodiments, the cotton fibers can comprise by dry weight, 0.7% to 1.6% ash, 0.4% to 1.0% wax, 0.1% to 1.0% sugar, and 0.5% to 1.0% organic acid.

In some embodiments, the cellulose of the cotton fibers of the cotton (or engineered cotton) as described herein can comprise a threshold amount of crystalline cellulose by dry weight of the cellulose. In some embodiments, an amount of the crystalline cellulose in the cellulose can be measured by X-ray diffraction. In some embodiments, the cellulose of the cotton fibers can comprise, by dry weight, at least 65% crystalline cellulose, at least 70% crystalline cellulose, at least 75% crystalline cellulose, at least 80% crystalline cellulose, at least 85% crystalline cellulose, at least 90% crystalline cellulose, or at least 95% crystalline cellulose. In some embodiments, the cellulose of the cotton fibers can comprise at least 80% by dry weight crystalline cellulose as measured by X-ray diffraction.

In some embodiments, the cotton fibers of the cotton (or engineered cotton) as described herein can have an average strength. The average strength of the cotton fibers can be measured by a Pressley test. In some embodiments, the average strength of the cotton fibers can be measured by a zero gauge Pressley test. In some embodiments, the average strength of the cotton fibers can be measured by a ⅛-inch gauge Pressley test. A Pressley test can be performed using a Pressley tester. The Pressley tester can be a balance type tester. (The Pressley tester can comprise a beam having side A and side B, pivoted at point O. A cotton fiber can be connected at one end to side B and at another end to a clamp. The beam can be positioned initially slightly inclined, such that side B can be slightly higher than side A. A heavy rolling weight can roll down the beam toward side A, moving side B upwards. As side B rises, the clamp can move upwards. The position of the weight relative to the pivot point O and the length of side A at the point that the cotton fiber breaks can be used to calculate the strength of the cotton fiber.) The average strength of the cotton fibers can be measured by a high volume instrument (HVI) test. In some embodiments, the average strength of the cotton fibers can be measured by a ⅛-inch gauge HVI test.

In some embodiments, the cotton fibers described herein can have an average strength of, or of about, 50, 60, 65, 70, 75, 80, 85, 90, 95, or 100 Mega pounds per square inch (Mpsi), or a range between any two foregoing values. In some embodiments, the cotton fibers can have an average strength of at least 50 Mega pounds per square inch (Mpsi), at least 60 Mpsi, at least 70 Mpsi, at least 80 Mpsi, at least 90 Mpsi, or at least 100 Mpsi. In some embodiments, the cotton fibers can have an average strength of at most 50 Mega pounds per square inch (Mpsi), at most 60 Mpsi, at most 70 Mpsi, at most 80 Mpsi, at most 90 Mpsi, or at most 100 Mpsi. In some embodiments, the cotton fibers described herein can have an average strength of, or of about, 10, 11, 12, 13, 14, 15, 16, 17, 18, 19, 20 grams per tex (g/tex), or a range between any two foregoing values. In some embodiments, the cotton fibers described herein can have an average strength of at least 10 grams per tex (g/tex), at least 11 g/tex, at least 12 g/tex, at least 13 g/tex, at least 14 g/tex, at least 15 g/tex, at least 16 g/tex, at least $1^7$ g/tex, at least 18 g/tex, at least 19 g/tex, or at least 20 g/tex. In some embodiments, the cotton fibers described herein can have an average strength of at most 10 grams per tex (g/tex), at most 11 g/tex, at most 12 g/tex, at most 13 g/tex, at most 14 g/tex, at most 15 g/tex, at most 16 g/tex, at most 17 g/tex, at most 18 g/tex, at most 19 g/tex, or at most 20 g/tex. In some embodiments, the cotton fibers can have an average strength of at least 70 Mega pounds per square inch (Mpsi). In some embodiments, the cotton fibers can have an average strength of at least 70 Mega pounds per square inch (Mpsi) as measured by a zero gauge Pressley test. In some embodiments, the cotton fibers can have an average strength of at least 15 grams per tex (g/tex). In some embodiments, the cotton fibers can have an average strength of at least 15 grams per tex (g/tex) as measured by a ⅛-inch gauge Pressley test. In some embodiments, the cotton fibers can have an average strength of at least 15 grams per tex (g/tex) as measured by a ⅛-inch gauge HVI test.

Kits

Provided herein, in some embodiments, are kits that can be utilized in preparation of a plant cell composition (such as one described hereinabove in the COMPOSITIONS section or described anywhere else herein) or in a method for preparing a plant cell composition (such as any method described hereinbelow in the METHODS section or described anywhere else herein). The kits can comprise materials, ingredients, buffers, and/or reagents to implement such methods or to prepare such plant cell compositions. In some embodiments, the kit can comprise a plant cell composition as described above. The plant cell composition of the kit can, for example, be used to seed a method described hereinbelow or described anywhere else herein using the kit. In some embodiments, the kit can comprise a medium or a plurality of media. In some cases, the kit can comprise ingredients and/or components for preparing a medium or a plurality of media. The medium or the plurality of media can comprise one or more media selected from the group consisting of a callus induction medium (or an induction medium), a callus growth medium (or a callus medium), a cell culture medium (a multiplication medium), a recovery medium, an elongation medium, and a maturation medium. The medium or the plurality of media can comprise one or more media selected from the group consisting of a callus induction medium (or an induction medium), a callus growth medium (or a callus medium), a cell culture medium (a multiplication medium), and a recovery medium. The medium or the plurality of media can comprise one or more media selected from the group consisting of a cell culture medium (a multiplication medium), a recovery medium, an elongation medium, and a maturation medium. The medium or the plurality of media can comprise one or more media described hereinbelow in this section entitled "KITS" or described anywhere else herein.

Callus Induction Medium

Some embodiments described herein are related to an induction medium or callus induction medium. In some embodiments, the callus induction medium described herein can be configured to facilitate division of at least a subset of cells of a plant explant (such as described hereinabove in the Plant Explant section or described anywhere else herein). For example, the callus induction medium can facilitate or promote induction of a cotton plant callus. The callus induction medium can comprise a diluted basal medium (i.e., from 1:1.5 to 1:5, from 1:1.5 to 1:4, from 1:1.5 to 1:3, etc.). The callus induction medium can comprise one or more salts, macronutrients, micronutrients, organic molecules, and/or hormones (such as those that can facilitate or promote induction). In some embodiments, the callus induction medium can be a liquid at about 25° C. In some embodiments, the callus induction medium can be not a liquid at a specified temperature. In some embodiments, the callus induction medium can be not a liquid at about 25° C. In some embodiments, the callus induction medium can be a semi-solid medium (such as gelled) at 25° C. Non-limiting examples of a semi-solid medium include soft agar, soft agarose, soft methylcellulose, or other soft polymeric gels. In some embodiments, the callus induction medium can comprise agar. In some embodiments, the callus induction medium can be agar-free. In some embodiments, the callus induction medium that is agar-free can be a liquid. In some embodiments, the callus induction medium that is agar-free can be a solid. In some embodiments, the callus induction medium that is agar-free can be a gel. In some embodiments, the callus induction medium that is agar-free can comprise an agar-substitute. In some embodiments, the callus induction medium can have a pH. The pH of the callus induction medium can be appropriate for induction of a plant callus (such as described hereinabove in the Plant Callus section or described anywhere else herein). In some embodiments, the pH of the callus induction medium can be optimized for induction of a plant callus (such as described hereinabove in the Plant Callus section or described anywhere else herein). In some embodiments, the pH of the callus induction medium can be from 5.3 to 6.3. In some embodiments, the pH of the callus induction medium can be, or be about, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or a range between any two foregoing values. In some embodiments, the callus induction medium can be utilized in a method described hereinbelow in the METHODS section or described anywhere else herein (such as the methods for preparing a plant cell composition).

Callus Growth Medium

Some embodiments described herein are related to a callus medium or callus growth medium. In some embodiments, the callus growth medium described herein can facilitate or promote growth of a plant callus (such as described hereinabove in the Plant Callus section or described anywhere else herein) or/and produce a proliferating cell aggregate (such as described hereinabove in the Proliferating Cell Aggregate section or described anywhere else herein). The callus growth medium can be a gel medium, and in some embodiments, can comprise agar and a mixture of macronutrients and micronutrients for the plant type of the plant callus (such as described hereinabove in the Plant Callus section or described anywhere else herein). In some cases, the callus medium can be enriched with nitrogen, phosphorus, or potassium. In some cases, a callus growth medium can be a liquid medium. In some embodiments, the callus growth medium can comprise at least one plant hormone or growth regulator (including auxins, gibberillins, etc.), or at least two plant hormones or growth regulators, or at least three plant hormones or growth regulators, or at least four plant hormones or growth regulators, or at least five plant hormones or growth regulators, or at least six plant hormones or growth regulators, or at least seven plant hormones or growth regulators, or at least eight plant hormones or growth regulators. The at least one plant hormone or plant growth regulator (or at least two, at least three, at least four, at least five, or at least six plant hormones or plant growth regulators) (including auxins, gibberillins, etc.) can be any one or combination selected from the group consisting of indole acetic acid (IAA), Indoyl-3-acrylic acid, 4-Cl-Indoyl-3-acetic acid, Indoyl-3-acetylaspartate, indole-3-acetaldehyde, indole-3-acetonitrile, indole-3-lactic acid, indole-3-propionic acid, indole-3-pyruvic acid, indole butyric acid (IBA), 2,4-dichlorophenoxyacetic acid (2,4 D), tryptophan, phenylacetic acid (PAA), Glucobrassicin, naphthaleneacetic acid (NAA), picloram (PIC), Dicamba, ethylene, para-chlorophenoxyacetic acid (pCPA), β-naphthoxyacetic acid (NOA), benzo(b)selenienyl-3 acetic acid, 2-benzothiazole acetic acid (BTOA), N6-(2-isopentenyl)adenine (2iP), zeatin (ZEA), dihydro-Zeatin, Zeatin riboside, kinetin (KIN), 6-(benzyladenine)-9-(2-tetrahydropyranyl)-9H-purine, 2,4,5,-trichlorophenoxyacetic acid (2,4,5-T), 6-benzylaminopurine (6BA), 1,3-diphenylurea, N-(2-chloro-4-pyridyl)-N'-phenylurea, (2,6-dichloro-4-pyridyl)-N'-phenylurea, N-phenyl-N'-1,2,3-thiadiazol-5-ylurea, gibberellin $A_5$, gibberellin A1 (GA1), gibberellic acid (GA3), gibberellin A4 (GA4), gibberellin A7 (GA7), brassinolide (BR), jasmonic acid (JA), gibberellin $A_8$, gibberellin $A_{32}$, gibberellin $A_9$, 15-β-OH-gibberellin $A_3$, 15-β-OH-gibberellin $A_5$, 12-β-OH-gibberellin $A_5$, 12-β-gibberellin $A_5$, salicylic acid, (−) jasmonic acid, (+)-7-iso-jasmonic acid, putrescine, spermidine, spermine, oligosaccharins, and stigmasterol. The at least one plant hormone or plant growth regulator (or at least two, at least three, at least four, at least five, or at least six plant hormones or plant growth regulators) (including auxins, gibberillins, etc.) can be any one or combination selected from the group consisting of indoyl-3-acetic acid, indoyl-3-acrylic acid, indoyl-3-butyric acid, 4-Cl-Indoyl-3-acetic acid, Indoyl-3-acetylaspartate, indole-3-acetaldehyde, indole-3-acetonitrile, indole-3-lactic acid, indole-3-propionic acid, indole-3-pyruvic acid, tryptophan, phenylacetic acid, Glucobrassicin, 2,4-dichlorophenoxyacetic acid, 1-naphthaleneacetic acid, Dicamba, Picloram, ethylene, benzo(b)selenienyl-3 acetic acid, trans-Zeatin, $N^6$-(2-isopentyl)adenine, dihydro-Zeatin, Zeatin riboside, Kinetin, benzylamide, 6-(benzyladenine)-9-(2-tetrahydropyranyl)-9H-purine, 1,3-diphenylurea, N-(2-chloro-4-pyridyl)-

N'-phenylurea, (2,6-dichloro-4-pyridyl)-N'-phenylurea, N-phenyl-N'-1,2,3-thiadiazol-5-ylurea, Gibberellin $A_1$, Gibberellin $A_3$, Gibberellin $A_4$, Gibberellin $A_5$, Gibberellin $A_7$, Gibberellin $A_8$, Gibberellin $A_{32}$, Gibberellin $A_9$, 15-β-OH Gibberellin $A_3$, 15-β-OH Gibberellin $A_5$, 12-β-OH Gibberellin $A_5$, 12-α-Gibberellin $A_5$, salicylic acid, jasmonic acid, (−) jasmonic acid, (+)-7-iso-jasmonic acid, putrescine, spermidine, spermine, oligosaccharins, brassinolide, and stigmasterol. The at least one plant hormone or plant growth regulator (or at least two, at least three, at least four, at least five, or at least six plant hormones or plant growth regulators) (including auxins, gibberillins, etc.) can be any one or combination selected from the group consisting of indole acetic acid (IAA), indole butyric acid (IB A), 2,4-dichlorophenoxyacetic acid (2,4 D), naphthaleneacetic acid (NA A), para-chlorophenoxyacetic acid (pCPA), β-naphthoxyacetic acid (NOA), 2-benzothiazole acetic acid (BTOA), picloram (PIC), 2,4,5,-trichlorophenoxyacetic acid (2,4,5-T), phenylacetic acid (PAA), kinetin (KIN), 6-benzylaminopurine (6BA), N6-(2-isopentenyl) adenine (2iP), zeatin (ZEA), gibberellin A1 (GA1), gibberellic acid (GA3), gibberellin A4 (GA4), gibberellin A7 (GA7), ethylene, brassinolide (BR), and jasmonic acid (JA).

In some embodiments, the callus growth medium can be a liquid at about 25° C. In some embodiments, the callus growth medium can be not a liquid at about 25° C. In some embodiments, the callus growth medium can be a semi-solid medium (such as gelled) at 25° C. Non-limiting examples of a semi-solid medium include soft agar, soft agarose, soft methylcellulose, or other soft polymeric gels. In some embodiments, the callus growth medium can comprise agar. In some embodiments, the callus growth medium can be agar-free. In some embodiments, the callus growth medium that is agar-free can be a liquid. In some embodiments, the callus growth medium that is agar-free can be a solid. In some embodiments, the callus growth medium that is agar-free can be a gel. In some embodiments, the callus growth medium that is agar-free can comprise an agar-substitute.

In some embodiments, the callus growth medium can have a pH. The pH of the callus growth medium can be appropriate for growing a plant callus (such as described hereinabove in the Plant Callus section or described anywhere else herein) or/and producing a proliferating cell aggregate (such as described hereinabove in the Proliferating Cell Aggregate section or described anywhere else herein). In some embodiments, the pH of the callus growth medium can be optimized for growing a plant callus (such as described hereinabove in the Plant Callus section or described anywhere else herein) or/and producing a proliferating cell aggregate (such as described hereinabove in the Proliferating Cell Aggregate section or described anywhere else herein). In some embodiments, the pH of the callus growth medium can be from 5.3 to 6.3. In some embodiments, the pH of the callus growth medium can be, or be about, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or a range between any two foregoing values. In some embodiments, the callus growth medium can be utilized in a method described hereinbelow in the METHODS section or described anywhere else herein (such as the methods for preparing a plant cell composition).

Cell Culture Medium

Some embodiments described herein are related to a cell culture medium (e.g., a multiplication medium). In some embodiments, the cell culture medium described herein can facilitate or promote proliferation of a cell population, or a proliferating cell aggregate (such as described hereinabove in the Proliferating Cell Aggregate section or described anywhere else herein). The cell culture medium can comprise one or more salts, macronutrients, micronutrients, organic molecules, and/or hormones (such as those that can facilitate or promote proliferation). In some cases, the cell culture medium can be configured to proliferate a cell population, such as a proliferating cell aggregate (such as described hereinabove in the Proliferating Cell Aggregate section or described anywhere else herein). The cell culture medium can comprise an enzyme that can degrade a plant cell wall of a plant cell of a cell population, or a proliferating cell aggregate (such as described hereinabove in the Proliferating Cell Aggregate section or described anywhere else herein). In some embodiments, the enzyme can be a pectocellulolytic enzyme. In some embodiments, the enzyme can comprise cellulase, hemicellulose, cellulysin, or a combination thereof. In some embodiments, the cell culture medium can have a pH. The pH of the cell culture medium can be appropriate for culturing a cell population, or a proliferating cell aggregate (such as described hereinabove in the Proliferating Cell Aggregate section or described anywhere else herein).

In some embodiments, the pH of the cell culture medium can be optimized for culturing a cell population, such as a proliferating cell aggregate (such as described hereinabove in the Proliferating Cell Aggregate section or described anywhere else herein). In some embodiments, the pH of the cell culture medium can be optimized for cell division. In some embodiments, the pH of the cell culture medium can be from 5.3 to 6.3. In some embodiments, the pH of the cell culture medium can be, or be about, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or a range between any two foregoing values. In some embodiments, the cell culture medium can have a different pH than a callus growth medium (such as described hereinabove in the Callus Growth Medium section or described anywhere else herein). In some embodiments, the cell culture medium can have a same pH as a callus growth medium (such as described hereinabove in the Callus Growth Medium section or described anywhere else herein). In some embodiments, the pH of the cell culture medium can differ from a pH of a callus growth medium (such as described hereinabove in the Callus Growth Medium section or described anywhere else herein) by less than 0.1, less than 0.2, or less than 0.3 units. For example, the pH of a cell culture medium can differ from a pH of a callus growth medium by less than 0.2 units. In some embodiments, the cell culture medium can be utilized in a method described hereinbelow in the METHODS section or described anywhere else herein (such as the methods for preparing a plant cell composition).

Recovery Medium

Some embodiments described herein are related to a recovery medium. In some embodiments, the recovery medium described herein can be a medium that can facilitate or promote recovery of cotton cells. The recovery medium can comprise one or more salts, macronutrients, micronutrients, organic molecules, and/or hormones that can facilitate or promote elongation. In some embodiments, the recovery medium can be utilized in a method described hereinbelow in the METHODS section or described anywhere else herein (such as the methods for preparing a plant cell composition or the methods of producing cotton).

Elongation Medium

Some embodiments described herein are related to an elongation medium. The elongation medium described herein can facilitate or promote elongation of cells capable of being elongated, for example, elongation of cotton cells. The elongation medium described herein can comprise one or more salts, macronutrients, micronutrients, organic molecules, and/or hormones (such as those that can facilitate or promote elongation). In some embodiments, the elongation medium can be configured to facilitate a release of a phenolic compound from a vacuole from a cotton cell. In some embodiments, the phenolic compound (such as O-diphenol) is configured to initiate fiber differentiation by inhibiting indoleacetic acid (IAA) oxidase and/or increase an intracellular auxin level. In some embodiments, the elongation medium can comprise at least one plant hormone or growth regulator (including auxins, gibberillins, etc.), or at least two plant hormones or growth regulators, or at least three plant hormones or growth regulators, or at least four plant hormones or growth regulators, or at least five plant hormones or growth regulators, or at least six plant hormones or growth regulators, or at least seven plant hormones or growth regulators, or at least eight plant hormones or growth regulators. The at least one plant hormone or plant growth regulator (or at least two, at least three, at least four, at least five, or at least six plant hormones or plant growth regulators) (including auxins, gibberillins, etc.) can be any one or combination selected from the group consisting of indole acetic acid (IAA), Indoyl-3-acrylic acid, 4-Cl-Indoyl-3-acetic acid, Indoyl-3-acetyl aspartate, indole-3-acetaldehyde, indole-3-acetonitrile, indole-3-lactic acid, indole-3-propionic acid, indole-3-pyruvic acid, indole butyric acid (IBA), 2,4-dichlorophenoxyacetic acid (2,4 D), tryptophan, phenylacetic acid (PAA), Glucobrassicin, naphthaleneacetic acid (NAA), picloram (PIC), Dicamba, ethylene, para-chlorophenoxyacetic acid (pCPA), β-naphthoxyacetic acid (NOA), benzo(b)selenienyl-3 acetic acid, 2-benzothiazole acetic acid (BTOA), N6-(2-isopentenyl) adenine (2iP), zeatin (ZEA), dihydro-Zeatin, Zeatin riboside, kinetin (KIN), 6-(benzyladenine)-9-(2-tetrahydropyranyl)-9H-purine, 2,4,5,-trichlorophenoxyacetic acid (2,4,5-T), 6-benzylaminopurine (6BA), 1,3-diphenylurea, N-(2-chloro-4-pyridyl)-N'-phenylurea, (2,6-dichloro-4-pyridyl)-N'-phenylurea, N-phenyl-N'-1,2,3-thiadiazol-5-ylurea, gibberellin $A_5$, gibberellin A1 (GA1), gibberellic acid (GA3), gibberellin A4 (GA4), gibberellin A7 (GA7), brassinolide (BR), jasmonic acid (JA), gibberellin $A_8$, gibberellin $A_{32}$, gibberellin $A_9$, 15-β-OH-gibberellin $A_3$, 15-β-OH-gibberellin $A_5$, 12-β-OH-gibberellin $A_5$, 12-α-gibberellin $A_5$, salicylic acid, (–) jasmonic acid, (+)-7-iso-jasmonic acid, putrescine, spermidine, spermine, oligosaccharins, and stigmasterol. The at least one plant hormone or plant growth regulator (or at least two, at least three, at least four, at least five, or at least six plant hormones or plant growth regulators) (including auxins, gibberillins, etc.) can be any one or combination selected from the group consisting of indoyl-3-acetic acid, indoyl-3-acrylic acid, indoyl-3-butyric acid, 4-Cl-Indoyl-3-acetic acid, Indoyl-3-acetyl aspartate, indole-3-acetaldehyde, indole-3-acetonitrile, indole-3-lactic acid, indole-3-propionic acid, indole-3-pyruvic acid, tryptophan, phenylacetic acid, Glucobrassicin, 2,4-Dichlorophenoxyacetic acid, 1-naphthaleneacetic acid, Dicamba, Picloram, ethylene, benzo(b)selenienyl-3 acetic acid, trans-Zeatin, $N_6$-(2-isopentyl)adenine, dihydro-Zeatin, Zeatin riboside, Kinetin, benzylamide, 6-(benzyladenine)-9-(2-tetrahydropyranyl)-9H-purine, 1,3-diphenylurea, N-(2-chloro-4-pyridyl)-N'-phenylurea, (2,6-dichloro-4-pyridyl)-N'-phenylurea, N-phenyl-N'-1,2,3-thiadiazol-5-ylurea, Gibberellin $A_1$, Gibberellin $A_3$, Gibberellin $A_4$, Gibberellin $A_5$, Gibberellin $A_7$, Gibberellin $A_8$, Gibberellin $A_{32}$, Gibberellin $A_9$, 15-β-OH Gibberellin $A_3$, 15-β-OH Gibberellin $A_5$, 12-β-OH Gibberellin $A_5$, 12-α-Gibberellin $A_5$, salicylic acid, jasmonic acid, (–) jasmonic acid, (+)-7-iso-jasmonic acid, putrescine, spermidine, spermine, oligosaccharins, brassinolide, and stigmasterol. The at least one plant hormone or plant growth regulator (or at least two, at least three, at least four, at least five, or at least six plant hormones or plant growth regulators) (including auxins, gibberillins, etc.) can be any one or combination selected from the group consisting of indole acetic acid (IAA), indole butyric acid (IBA), 2,4-dichlorophenoxyacetic acid (2,4 D), naphthaleneacetic acid (NAA), para-chlorophenoxyacetic acid (pCPA), β-naphthoxyacetic acid (NOA), 2-benzothiazole acetic acid (BTOA), picloram (PIC), 2,4,5,-trichlorophenoxyacetic acid (2,4,5-T), phenylacetic acid (PAA), kinetin (KIN), 6-benzylaminopurine (6BA), N6-(2-isopentenyl) adenine (2iP), zeatin (ZEA), gibberellin A1 (GA1), gibberellic acid (GA3), gibberellin A4 (GA4), gibberellin A7 (GA7), ethylene, brassinolide (BR), and jasmonic acid (JA).

In some embodiments, the elongation medium can have a pH. The pH of the elongation medium can be appropriate for producing/inducing an elongated cell, such as an elongated cotton cell or a plurality of elongated cotton cells (such as described hereinbelow or described anywhere else herein). In some embodiments, the pH of the elongation medium can be optimized for cell elongation (such as cotton cell elongation). In some embodiments, the pH of the elongation medium can be from 5.3 to 6.3. In some embodiments, the pH of the elongation medium can be, or be about, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or a range between any two foregoing values. In some embodiments, the elongation medium can be utilized in a method described hereinbelow in the METHODS section or described anywhere else herein (such as the methods for producing cotton). In some embodiments, the elongation medium can be utilized in preparing an engineered cotton, such as described hereinabove in the section entitled "Engineered Cotton" or described anywhere else herein.

Maturation Medium

Some embodiments described herein are related to a maturation medium. In some embodiments, the maturation medium described herein can facilitate or promote maturation of cells, such as maturation of cotton cells. The maturation medium can comprise one or more salts, macronutrients, micronutrients, organic molecules, and/or hormones (such as those that can facilitate or promote maturation). In some embodiments, the maturation medium can comprise a maturation reagent. In some embodiments, the maturation reagent of the maturation medium can be a wall-regeneration reagent. In some embodiments, the maturation medium can be utilized in a method described hereinbelow in the METHODS section or described anywhere else herein (such as the methods for producing cotton). In some embodiments, the maturation medium can be utilized in preparing an engineered cotton, such as described hereinabove in the section entitled "Engineered Cotton" or described anywhere else herein.

Instructions

In some embodiments, the kit can comprise instructions for preparing a medium or a plurality of media (such as any provided hereinabove in the K ITS section or described anywhere else herein). In some embodiments, the kit can comprise instructions for implementing one or more methods (such as those provided hereinbelow in the METHODS section, any subset thereof, any combination thereof, or any derivative thereof). In some cases, the kit can comprise instructions for cell preparation, cryopreservation, cell recovery, bioreactor inoculation, elongation of cells, separation and/or isolation of elongated cells, maturation of cells, drying of fibers after maturation, recycling cells, or a combination thereof.

Methods

Methods provided hereinbelow, in some embodiments, in the METHODS section can be utilized for preparing a plant cell composition (such as described hereinabove in the COMPOSITIONS section or described anywhere else herein) or for producing cotton (such as described hereinabove in the COMPOSITIONS section or described anywhere else herein). In some embodiments, the methods for preparing the plant cell composition or producing cotton utilize a medium or a plurality of media (such as described hereinabove in the KITS section or described anywhere else herein).

Methods for Preparing Plant Cell Compositions

Provided herein, in some embodiments, are methods for preparing a plant cell composition. In some embodiments, such methods can be utilized to prepare a plant cell composition, such as described hereinabove in the section entitled "Plant Cell Compositions" or described anywhere else herein, or any one of the cell bank stocks as described hereinabove.

The method for preparing a plant cell composition can comprise (a) contacting a plant callus (such as described hereinabove in the section entitled "Plant Callus" or described anywhere else herein) with a callus growth medium (such as described hereinabove in the section entitled "Callus Growth Medium" or described anywhere else herein) under conditions sufficient to produce a proliferating cell aggregate (such as described hereinabove in the section entitled "Proliferating Cell Aggregate" or described anywhere else herein). In some embodiments, such contacting of (a) can comprise subculturing the plant callus on the callus growth medium. In some embodiments, such contacting can comprise subculturing the plant callus for at least 2 passages on the callus growth medium. The at least 2 passages of subculturing on the callus growth medium can comprise from two to ten passages. In some embodiments, the plant callus can be subcultured for at least 2, at least 3, at least 4, at least 5, at least 6, at least 7, at least 8, at least 9, at least 10, at least 11, at least 12, at least 13, at least 14, or at least 15 passages. In some embodiments, the plant callus can be subcultured for about 2, about 3, about 4, about 5, about 6, about 7, about 8, about 9, about 10, about 11, about 12, about 13, about 14, or about 15 passages, or a range between any two foregoing values.

In some embodiments of the method for preparing the plant cell composition, (a) can be performed at a given temperature. In some embodiments, the contacting of (a) can be performed at, or at about, 16° C., 18° C., 20° C., 22° C., 24° C., 26° C., 28° C., 30° C., 32° C., 34° C., 36° C., 38° C., or 40° C., or a range between any two foregoing values. In some embodiments, for example, each of the passages of the subculturing of (a) can be performed at a temperature of from 22° C. to 34° C. In some embodiments of the method for preparing the plant cell composition, each of the at least two passages of the subculturing of (a) can have a duration of, or of about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two foregoing values. For example, in some embodiments, each of the at least two passages of subculturing of (a) can have a duration of from 15 to 32 days.

The method for preparing the plant cell composition, as described in the immediately preceding paragraph, can further comprise (b) contacting the proliferating cell aggregate (such as described hereinabove in the section entitled "Proliferating Cell Aggregate" or described anywhere else herein) with a cell culture medium (such as described hereinabove in the section entitled "Cell Culture Medium" or described anywhere else herein) under conditions sufficient to produce a plant cell composition comprising a plurality of cells (such as described hereinabove in the section entitled "Plant Cell Composition" or described anywhere else herein). In some embodiments of the method for preparing the plant cell composition, such contacting of (b) can comprise subculturing the proliferating plant cell for at least two passages in the cell culture medium. The at least two passages of subculturing in the cell culture medium can comprise from two to ten passages. In some embodiments, the proliferating cell aggregate can be subcultured for at least 2, at least 3, at least 4, at least 5, at least 6, at least 7, at least 8, at least 9, at least 10, at least 11, at least 12, at least 13, at least 14, or at least 15 passages. In some embodiments, the proliferating cell aggregate can be subcultured for about 2, about 3, about 4, about 5, about 6, about 7, about 8, about 9, about 10, about 11, about 12, about 13, about 14, or about 15 passages, or a range between any two foregoing values. For example, in some embodiments, the proliferating cell aggregate can be subcultured from 2 to 10 passages in cell culture medium. In some embodiments of the method for preparing the plant cell composition, (b) can be performed at a given temperature. In some embodiments, the contacting of (b) can be performed at, or at about, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C., or a range between any two foregoing values. In some embodiments, for example, each of the passages of the subculturing of (b) can be performed at a temperature of from 28° C. to 40° C.

In some embodiments of the method for preparing the plant cell composition, each of the at least two passages of the subculturing of (b) can have a duration of, or of about, 5, 6, 7, 8, 9, 10, 11, 12, 13, 14, 15, 16, 17, 18, 19, 20, 21, 22, 23, 24, 25, 26, 27, 28, 29, or 30 days, or a range between any two foregoing values. For example, in some embodiments, each of the at least two passages of subculturing of (b) can have a duration of from 10 to 25 days. In some embodiments, each passage of the at least two passages of subculturing of (b) can be performed at a temperature higher than at which at least one passage of the at least two passages of subculturing of (a) is performed. In some embodiments, each passage of the at least two passages of subculturing of (b) can be performed at a temperature of about 1° C., about 2° C., about 3° C., about 4° C., about 5° C., about 6° C. about 7° C., about 8° C., about 9° C., about 10° C., or a range between any two foregoing values, higher than at which at least one passage of the at least two passages of subculturing of (a) is performed. In some embodiments, each passage of the at least two passages of subculturing of (b) can be performed at a temperature from 2° C. to 6° C. higher than at which at least one passage of the at least two passages of subculturing of (a) is performed. In some embodiments of the method for preparing the plant cell composition, (b) can further comprise (e.g., before, during, or after the contacting of (a)) sieving, filtering, separating, pipetting, or decanting cells of a proliferating cell aggregate or a derivative thereof to yield a plant cell composition (such as described hereinabove in the section entitled "Plant Cell Composition" or described anywhere else herein).

In some embodiments, the method of preparing the plant cell described herein, can be preceded by (c) contacting a plant explant (such as described hereinabove in the section entitled "Plant Explant" or described anywhere else herein) with a callus induction medium (such as described hereinabove in the section entitled "Callus Induction Medium" or described anywhere else herein) under conditions sufficient to produce a plant callus (such as described hereinabove in the section entitled "Plant Callus" or described anywhere else herein).

Methods for Producing Cotton

Provided herein, in some embodiments, are methods for producing cotton or engineered cotton (such as described hereinabove in the section entitled "Engineered Cotton" or described anywhere else herein). The methods for producing cotton can be performed in vitro. In some cases, the methods for producing cotton can be performed in a bioreactor.

In some embodiments, the method for producing cotton as described herein can comprise (a) providing a reaction vessel comprising a solution comprising a plurality of cotton cells. In some embodiments, the method for producing cotton as described herein can further comprise (b), in the reaction vessel, contacting the solution comprising the plurality of cotton cells with an elongation medium (such as described hereinabove in the section entitled "Elongation Medium" or described anywhere else herein) under conditions sufficient to induce at least a portion of the plurality of cotton cells to elongate to yield a plurality of elongated cotton cells, thereby producing cotton (such as described hereinabove in the section entitled "Engineered Cotton" or described anywhere else herein). In some embodiments, an elongated cell of the plurality of elongated cotton cells can have a first dimension that is greater than a second dimension of the elongated cell. In some embodiments. (b) results in at least 10%, at least 20%, at least 30%, at least 40%, at least 50%, at least 60%, at least 70%, at least 80%, or at least 90% of the plurality of cotton cells of the solution to elongate. In some embodiments, about 10%, about 20%, about 30%, about 40%, about 50%, about 60%, about 70%, about 80%, about 90%, or a range between any two foregoing values, of the plurality of cotton cells of the solution to elongate. In some embodiments, an elongated cell (or a cotton fiber) of the plurality of elongated cotton cells can have a first dimension (e.g., a length) and a second dimension (e.g., a width). In some embodiments, the first dimension can be greater than the second dimension. In some embodiments, the first dimension can be at least 2 times, at least 10 times, at least 50 times, at least 100 times, at least 500 times, or at least 1,000 times greater than the second dimension. Elongation can be performed at a given temperature or temperature range. In some embodiments, elongation can be performed at room temperature. In some embodiments, elongation can be performed at about 20° C., about 22° C., about 24° C., about 26° C., about 28° C., about 30° C., about 32° C., about 34° C., about 36° C., about 38° C., about 40° C., about 42° C., about 44° C., about 46° C., about 48° C., about 50° C., or a range between any two foregoing values. In some embodiments, elongation can be performed at a temperature from about 28° C. to about 40° C.

In some embodiments, the method for producing cotton as described herein can further comprise (c) subjecting the plurality of elongated cotton cells to conditions sufficient to mature the plurality of elongated cotton cells to yield the cotton (such as described hereinabove in the "Engineered Cotton" section or described anywhere else herein). In some embodiments, (c) comprises contacting the plurality of elongated cotton cells with a maturation medium (such as described hereinabove in the "Maturation Medium" section or described anywhere else herein) under conditions sufficient to yield a plurality of mature elongated cotton cells. In some embodiments, (c) further comprises drying the plurality of mature elongated cotton cells to yield the cotton (such as described hereinabove in the "Engineered Cotton" section or described anywhere else herein). Drying can comprise air drying, drying using a vacuum apparatus, drying under an air flow, drying under flow of a gas (e.g., nitrogen or argon), drying using heat, or freeze drying.

In some embodiments of the method for producing cotton as described herein, (b) can further comprise separating the plurality of elongated cells from a remainder of the plurality of cotton cells or derivatives thereof. In some cases, such separation can comprise separation of elongated cells from non-elongated cells. In some embodiments, only elongated cells above a threshold length are separated. For example, elongated cells that are at least 2, at least 5, at least 10, at least 50, at least 100, at least 500, at least 1,000, at least 5,000, or at least 10,000 times longer in a first dimension than in a second dimension can be separated. Separation can be accomplished by any acceptable method. In some cases, separating can comprise filtering, sieving, decanting, centrifuging, or a combination thereof. In some cases, all elongated cells can be separated. In some cases, at least about 75%, at least about 80%, at least about 85%, at least about 90%, at least about 95%, or at least about 99% of elongated cells can be separated.

In some embodiments, the method for producing cotton as described herein can comprise removing the remainder of the plurality of cotton cells. For example, cotton cells that have not been elongated can be removed. Such removal can be part of a separation step or protocol. In some embodiments, a cotton cell in the remainder of cotton cells can have a first dimension that is less than a first dimension of one or more of the elongated cotton cells. For example, a cotton cell in the remainder of cotton cells can have a length that is less than the length of the elongated cotton cells. In some embodiments, a cotton cell in the remainder of cotton cells can be partially elongated. In some embodiments, a cotton cell in the remainder of cotton cells can be not elongated. In some embodiments, at least a portion of the remainder of the plurality of cotton cells (e.g., removed non elongated cotton cells) can be recycled.

In some embodiments, the method for producing cotton as described herein can comprise recycling at least a portion of the remainder of the plurality of cotton cells. In some cases, recycling can comprise subjecting the cotton cells to a method again. In some cases, recycling can comprise culturing the cotton cells to produce more cotton cells. In some cases, recycling can comprise freezing or otherwise saving and/or preserving cotton cells for future use.

In some embodiments of the method of producing cotton, the cotton produced can have a dry mass of at least 10 grams per liter (g/L) fresh weight (FW). In some embodiments, the dry mass of the cotton (or engineered cotton) can be at least 50 grams per liter (g/L) fresh weight (FW). In some embodiments, the dry mass of the cotton (or engineered cotton) can be at least 100 grams per liter (g/L) fresh weight (FW). In some embodiments, the dry mass of the cotton (or engineered cotton) can be from 50 grams per liter (g/L) fresh weight (FW) to 500 g/L (FW). In some embodiments, the dry mass of the cotton (or engineered cotton) can be from 100 grams per liter (g/L) fresh weight (FW) to 500 g/L (FW). In some embodiments, the dry mass of the cotton (or engineered cotton) can be from 100 grams per liter (g/L)

fresh weight (FW) to 300 g/L (FW). In some embodiments, the cotton produced can have a dry mass of about 50 grams per liter (g/L) fresh weight (FW), about 100 g/L FW, about 200 g/L FW, about 300 g/L FW, about 400 g/L FW, about 500 g/L FW, at least 600 g/L FW, at least 700 g/L FW, at least 800 g/L FW, at least 900 g/L FW, or at least 1000 g/L FW, or a range between any of the foregoing values of cotton cells in a reaction vessel.

In some embodiments of the method of producing cotton, the cotton produced can have a dry mass of at least 50 milligrams (mg). In some embodiments, the cotton produced can have a dry mass of at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, or at least 1000 mg. In some embodiments, the cotton produced can have a dry mass of at least 1 gram (g), at least 5 g, at least 10 g, at least 50 g, at least 100 g, at least 500 g, at least 1 kg, at least 5 kg, at least 10 kg, at least 50 kg, or at least 100 kg.

In some embodiments of the method of producing cotton, the cotton produced can have a trash content below a given threshold. The trash content can be a non-lint substance. In some embodiments, the cotton produced can comprise at most 10% by dry weight of a trash content. In some embodiments, the cotton produced can comprise at most 5% by try weight of a trash content. In some embodiments, the cotton produced can comprise at most 1% by dry weight of a trash content. In some embodiments, the cotton produced can comprise at most 0.5% by dry weight of a trash content. In some embodiments, the cotton produced can comprise at most 0.1% dry weight of a trash content.

In some embodiments, the method of producing cotton can be performed in a given time period. In some embodiments of the method of producing cotton, the cotton can be produced from the solution comprising a plurality of cotton cells in a time period of at most 45 days. In some embodiments of the method of producing cotton, the cotton can be produced from the solution comprising a plurality of cotton cells in a time period of at most 41 days. In some embodiments of the method of producing cotton, the cotton can be produced from the solution comprising a plurality of cotton cells in a time period of at most 34 days. In some embodiments of the method of producing cotton, the cotton can be produced from the solution comprising a plurality of cotton cells in a time period of at most 30 days. In some embodiments of the method of producing cotton, the cotton can be produced from the solution comprising a plurality of cotton cells in a time period of, or of about, 45, 44, 43, 42, 41, 40, 39, 38, 37, 36, 35, 34, 33, 32, 31, 30, 29, 28, 27, 26, 25, 24, 23, 22, 21, or 20 days, or a range between any two of foregoing values. In some embodiments of the method of producing cotton, the cotton can be produced from the solution comprising a plurality of cotton cells in a time period of at least, or of at least about, 45, 44, 43, 42, 41, 40, 39, 38, 37, 36, 35, 34, 33, 32, 31, 30, 29, 28, 27, 26, 25, 24, 23, 22, 21, or 20 days. In some embodiments of the method of producing cotton, the cotton can be produced from the solution comprising a plurality of cotton cells in a time period of at most, or of at most about, 45, 44, 43, 42, 41, 40, 39, 38, 37, 36, 35, 34, 33, 32, 31, 30, 29, 28, 27, 26, 25, 24, 23, 22, 21, or 20 days. The time period in which the method for producing cotton is performed can comprise a LAG phase, a growth phase, an elongation phase, a maturation phase, or a combination thereof. In some embodiments, the time period can comprise all of a LAG phase, a growth phase, an elongation phase, and a maturation phase.

Bioreactors

Also provided herein are bioreactors configured to produce any one or more compositions provided hereinabove in the COMPOSITIONS section. Also provided herein are bioreactors configured to perform any one or more methods provided hereinabove in the METHODS section. A bioreactor can be configured to utilize components of a kit provided herein to produce a composition or carry out a method.

In some embodiments, a bioreactor can be configured to produce a cell bank stock. In some embodiments, a bioreactor can be configured to carry out a method for preparing a cell bank stock. In some such cases, a bioreactor can be configured to utilize components of a kit for preparation of a cell bank stock, such as a callus growth medium and/or a multiplication medium.

FIG. 1 provides a flow chart illustrating an example of different processes that can be performed by a bioreactor, and how these processes can be interconnected.

In some embodiments, a bioreactor can be configured to produce a cotton fiber. In some embodiments, a bioreactor can be configured to carry out a method for large scale cotton fiber production. In some embodiments, a bioreactor can be configured to carry out a method for rapid cotton fiber production. In some embodiments, a bioreactor can be configured to utilize components of a kit for large scale fiber production. In some embodiments, a bioreactor can be configured to utilize components of a kit for rapid fiber production.

In some embodiments, a bioreactor can be configured to produce engineered cotton. In some embodiments, a bioreactor can be configured to utilize components of a kit for production of engineered cotton, which can comprise elements of kits provided herein.

Computer Systems

Figure 2:
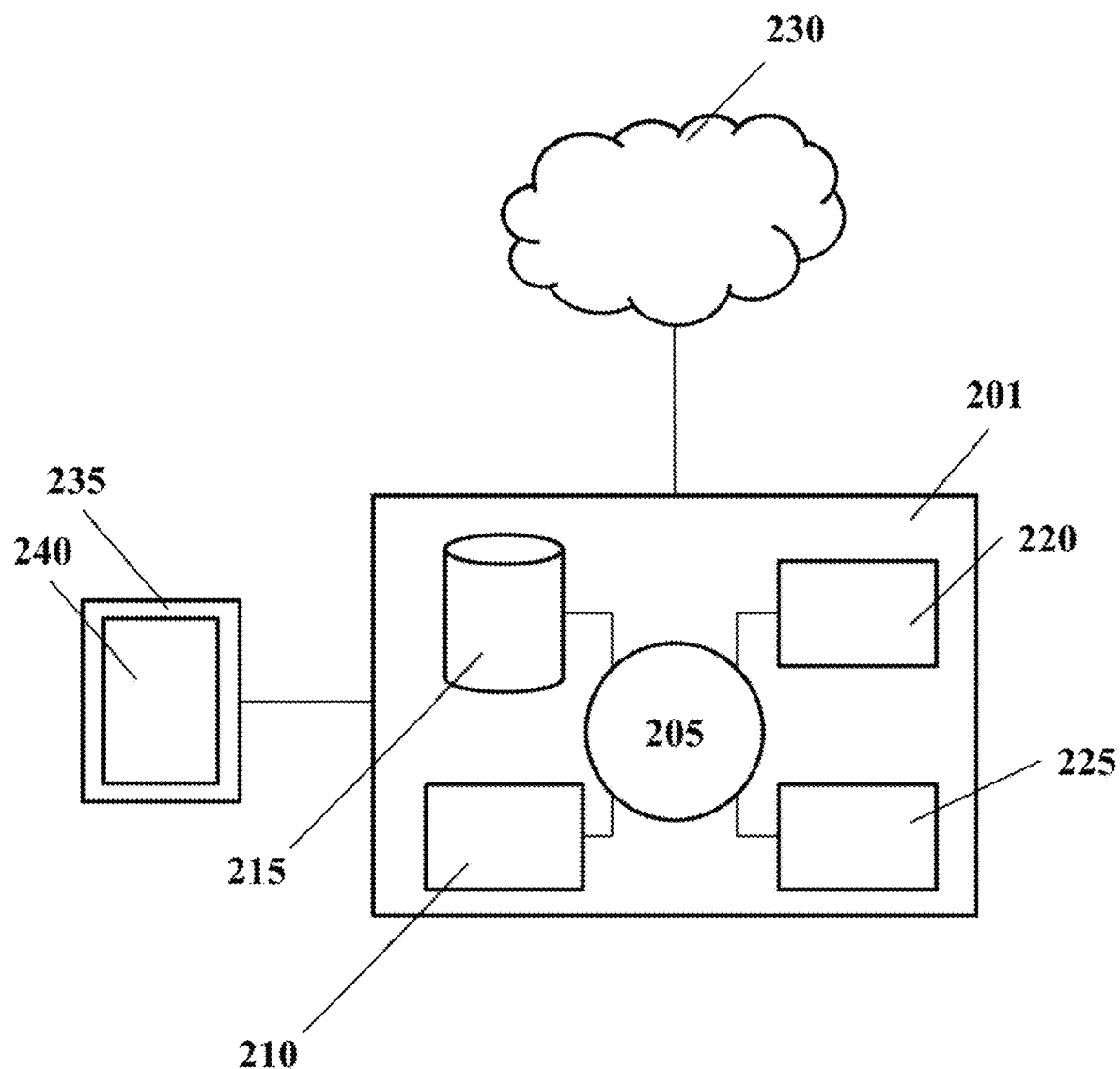
FIG. 2 shows a computer system that is programmed or otherwise configured to implement methods provided herein.

The present disclosure provides computer systems that are programmed to implement methods of the disclosure. FIG. 2 shows a computer system 201 that is programmed or otherwise configured to provide and/or implement instructions for or means of implementation of induction, callus growth, cell culture, elongation, or maturation. The computer system 201 can regulate various aspects of induction, callus growth, cell culture, elongation, or maturation of the present disclosure. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210) or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (EI) 240 for providing, for example, instructions for or means of implementation of induction, callus growth, cell culture, elongation, or maturation. Examples of ET's include, without limitation, a graphical user interface (GET) and web-based user interface.

Methods and systems of the present disclosure can be implemented by way of one or more algorithms. An algorithm can be implemented by way of software upon execution by the central processing unit 205. The algorithm can, for example, provide and/or execute instructions for or means of implementation of induction, callus growth, cell culture, elongation, or maturation.

EXAMPLES

Example 1: Preparation of a Plant Cell Composition

From a select plant (e.g., cotton), cells are isolated by placing sterilized explants from apical meristems, cotyledons, young leaves, hypocotyls, ovules, stems, mature leaves, flower, flower stalks, roots, bulbs, germinated seeds, and cambial meristematic cells (CMC) on a callus induction medium (e.g., a semi-solid basal salts medium) (for induction. The dedifferentiated masses formed are conditioned by passing three up to five subculturing at intervals of 21-26 days on a callus growth medium (e.g., a semi-solid basal salts medium) for growth.

After cell culture stabilization, cells from a soft or friable callus are transferred into a liquid medium to form a suspension cell. Suspensions are subcultured at intervals of 15-20 days for homogenization to provide fine cell suspension culture, by filtering, pipetting/decantation, or by addition of a low concentration of pectinase. The homogeneous nature of cells in these cultures give rise to reproducible and reliable results.

Example 2: Cryopreservation of Suspension-Cultured Cells

Cryopreservation techniques remove the need for frequent culturing and, thus, reduce the chance of microbial contamination. The protocol provided below allows the cryopreservation of over 100 cell lines simultaneously in a single day.

Suspension-cultured cells from *Gossypium* spp. and other species in exponentially growing phase are transferred to 15 ml tubes and centrifuged at 100×g for 1 min. Cell suspensions are handled using micropipettes with large orifice tips. The supernatant is removed, and cells are then suspended in cryoprotectant solution (LS: 2M glycerol, 0.4 M sucrose) supplemented with up to 100 mM L-proline at the cell density of 10% (v/v), and incubated at room temperature for 0-120 minutes with and without shaking at 60 rpm. Aliquots (0.5 ml) of cell suspensions are dispensed into cryovials (Fisher Scientific). Cryovials containing cell suspension in LS are cooled to −35° C. at a rate of −0.5, −1, or −2° C. min$^{-1}$ using a programmable freezer. After reaching −35° C., cells are kept at −35° C. for 0, 30, or 60 minutes, and then plunged into liquid nitrogen.

In vitro dedifferentiated plant cell suspension cultures are more convenient for large-scale production, as they offer the advantage of a simplified model system for the study of plants. Cell suspension cultures contain a relatively homogeneous cell population, allowing rapid and uniform access to nutrition, precursors, growth hormones, and signal compounds for the cells.

Example 3: Cell Recovery

The vials containing cryopreserved cells are transferred from the liquid nitrogen storage vessel into a Dewar flask containing liquid nitrogen. Each vial is transferred (one by one) to a clean 35-40° C. water bath and gently flipped several times until thawed (the last piece of ice disappears). Immediately, each vial is placed on ice again. Each vial is centrifuged at 100 g, at 4° C. for 1-2 min. The outside of each vial is wiped with 70% (vol/vol) ethanol and the supernatant from each vial is removed using a sterile Pasteur pipette. A sterile 3.5-ml transfer pipette is used to transfer two-thirds volume of the cells by spreading or placing them as a few clusters onto the filter paper. The dish is closed and sealed with Parafilm.

The dish(es) are covered with one or two sheets of filter paper to reduce the light intensity then placed in the culture room in regular conditions (24-26° C.). After 2 days of recovery, a spatula (width of 4 mm) is used to collect some cell mass (about 100-200 mg FW) from the plate and place into a microtube for viability testing. The remaining cells are transferred with the upper filter paper to a fresh recovery dish containing recovery medium. The dishes are closed and sealed, covered with filter paper, and then returned to the culture room.

Depending on their growth rates, cells are allowed to grow for an additional number of days in the same culture room, in regular conditions (24-26° C.). When most of the filter paper is covered with a thick layer of cells, the cell mass is transferred to a fresh dish containing recovery medium without filter paper for a further 1-2 weeks under standard conditions (at this recovery stage, agarose may be replaced by agar). After a recovery period of 3-9 weeks, cells are transferred to a liquid medium to initiate suspension culture.

Example 4: Bioreactor Inoculation

For inoculum, the medium is prepared with deionized (DI) water to make a total volume of 200 mL (1 L flask) and sterilized through autoclaving at 121° C. for 15 minutes. After cooling to room temperature, plant growth regulators and amino acids are added using a 0.2 µm pore size membrane filter. Twenty grams of cells are inoculated and maintained in a shaker in dark at a temperature from about 30° C. to about 35° C. at 80 rpm and left for inoculum growth. After 16 days (7 days of LAG phase and 9 days of exponential phase), the suspension is sufficiently dense for feeding the bioreactors (Titer=100 g L$^{-1}$ comparable a thick applesauce with no visible free medium).

An illustrative schematic of the bioreactor can be found in FIG. 1. The bioreactor is fed with in vitro cells, with sterilized medium, and air compression. The bioreactors are connected to the controller prior to inoculation, to stabilize pH 5.8 (±0.2) and to control and calibrate the flow of O$_2$. As illustrated in the flowchart in FIG. 1L the first vessel of the inoculum train occurs at a temperature from about 30° C. to about 35° C. with a 100 g L$^{-1}$ of cells at an exponential phase. In parallel, the sterilization of the culture medium occurs at approximately 125 to approximately 140° C. and returns (stream 16) to the heat exchanger (stream 13) to cooling the medium at a temperature from about 30° C. to about 35° C. (E-103). With this, the sterile medium is ready to feed the reactors of the multiplication area (reactors R-101 to R-104).

The air for cell oxygenation is also adjusted to the process temperature in the heat exchanger (E-105) and thus is split into four different streams (streams 27, 28, 29 and 31) that feed the inoculum train (reactors R-101 to R-104).

The multiplication occurs in a duration from 5 to 12 days for cells, and the duplication time is approximately 1 day to 3 days (depending on linage(s)). These times conclude when the cell amount increases, for example, 64 times. In the end, the content is loaded to the next reactor (R-102) and so on. The last reactor (R-104) has an adjacent lung tank, where after the reaction the contents are discharged in the batch feeding tank (Tq-101) with continuous output (stream 5). Thus, during the multiplication time of the R-104 reactor, the Tq-101 is continuously unloading the cells for the next stage, the separation, at a continuous flow rate.

Example 5: Elongation of Cells

For elongation, plant cells are separated from the medium using a decanter vessel (S-101) (stream 6) and the medium can be relocated for water treatment (stream 45), as illustrated in the flowchart in FIG. 1. The elongation growth medium is added to the reactors to sterilization by autoclaving at same conditions used in multiplication step and cooling at a temperature from about 30° C. to about 35° C. for cell differentiation.

Thus, the cells from the multiplication (stream 6) feed three elongation reactors (R-105, R-106, and R-107) are represented by the reactor block (R-105) in the flowchart in FIG. 1. Each reactor receives a third of the cells and the reaction volume comprises the cells (stream 6), medium (stream 38), and air (stream 32) flows.

Example 6: Separation and Isolation of Elongated Cells

After elongation according to Example 5, 3 tanks (Tq-102, Tq-103, and Tq-104) are fed, which in the flowchart in FIG. 1 are represented only by block Tq-102. Each tank, with volume slightly larger than those of the reactors, receives the substantially same volume of the three reactors. The output of the elongation tanks (stream 7) is routed to the second decanter (S-102). The bottom product (stream 8), comprising elongated and unelongated cells, is routed to the sieve (S-103), while the medium (stream 46) is removed to the effluent treatment. The function of the sieve is to remove unelongated and smaller cells that are not pre-fibers. The sieve (S-103) retains the elongated cells (pre-fibers) and releases all nonelongated cells (which will not become cotton fibers).

Example 7: Maturation and Drying of Cells

In the maturation stage, as well as in the multiplication and elongation stages, a sterilized medium is used. Maturation is recognized by secondary cell wall deposition. Sugars are combined to produce cellulose, which is the main component of cotton fiber (natural glucose polymerization) that occurs inside the cell forming the secondary wall. In this process, the density of pre-fiber increases from 1.05 to 1.55 g/ml, which is the density of cotton fiber.

After maturation time, the R-108 output is directed to the buffer tank Tq-105 (FIG. 1) to enable a continuous downstream process. In the sequence, the mid-fiber mixture (stream 10) is routed to the third decanter (S-104), where the cotton fibers (stream 11) are separated from the medium (stream 48). At this stage, the fibers produced have moisture content above acceptable level (10 to 20% in water mass). To reduce the moisture content, a drying process working with air is implemented. This air passes through the cotton fibers and part of the water is removed until a moisture content of at most 5% is reached.

Example 8: Recycling

In some embodiments, a composition created via a method described herein can be recycled. For example, in such a case, after completion of a method or step of a method, an aliquot of a composition is reserved and re-introduced into an earlier step in a method. In some cases, an aliquot of cells unsuccessful in induction, growth, elongation, or maturation is reserved and re-introduced into an earlier step in a method.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of producing cotton fibers from cotton callus cells in vitro, the method comprising the following steps in order:
   (1) culturing cotton callus cells in a suspension culture medium;
   (2) feeding a first bioreactor with the callus cells, a multiplication medium, and air compression;
   (3) culturing the callus cells in the first bioreactor for 5 to 12 days to accomplish at least two rounds of duplication of the callus cells;
   (4) serially repeating steps (2) and (3) one or more times, thereby obtaining serially duplicated cells;
   (5) seeding one or more second bioreactors with the serially duplicated cells, an elongation medium, and air compression;
   (6) culturing the serially duplicated cells in the one or more second bioreactors, thereby obtaining elongated cells; and
   (7) culturing the elongated cells in a maturation medium, thereby obtaining the cotton fibers.

2. The method according to claim 1, wherein during step (6) non-elongated cells are also obtained, of and wherein step (6) further comprises separating the elongated cells from the non-elongated cells.

3. The method according to claim 2, wherein the separating of step (6) comprises one or more of filtering, sieving, decanting, or centrifuging.

4. The method according to claim 1, wherein the culturing of step (7) is carried out in one or more third bioreactors.

5. The method according to claim 4, wherein step (6) further comprises seeding the one or more third bioreactors with the elongated cells, the maturation medium, and air compression.

6. The method according to claim 1, wherein the culturing of step (7) is carried out in the one or more second bioreactors.

7. The method according to claim 1, wherein the cotton callus cells have been obtained from cryopreserved suspension culture cells.

8. The method according to claim 7, wherein the cryopreserved suspension culture cells have been obtained from a suspension culture of cells from a soft or friable callus.

9. The method according to claim 8, wherein the soft or friable callus has been obtained by induction of sterilized explants from one or more of apical meristems, cotyledons, young leaves, hyopcotyls, ovules, stems, mature leaves, flower, flower stalks, roots, bulbs, germinated seeds, or cambial meristematic cells on a callus induction medium.

10. The method according to claim 1, wherein the cotton callus cells comprise one or more of *Gossypium anomalum, Gossypium arboreum, Gossypium armourianum, Gossypium barbadense, Gossypium herbaceum, Gossypium hirsutum, Gossypium klotzchianum*, and *Gossypium raimondii*.

11. The method according to claim 1, wherein the cotton callus cells comprise *Gossypium hirsutum*.

12. The method according to claim 1, wherein the cotton callus cells comprise *Gossypium barbadense*.

* * * * *